Figure 1:
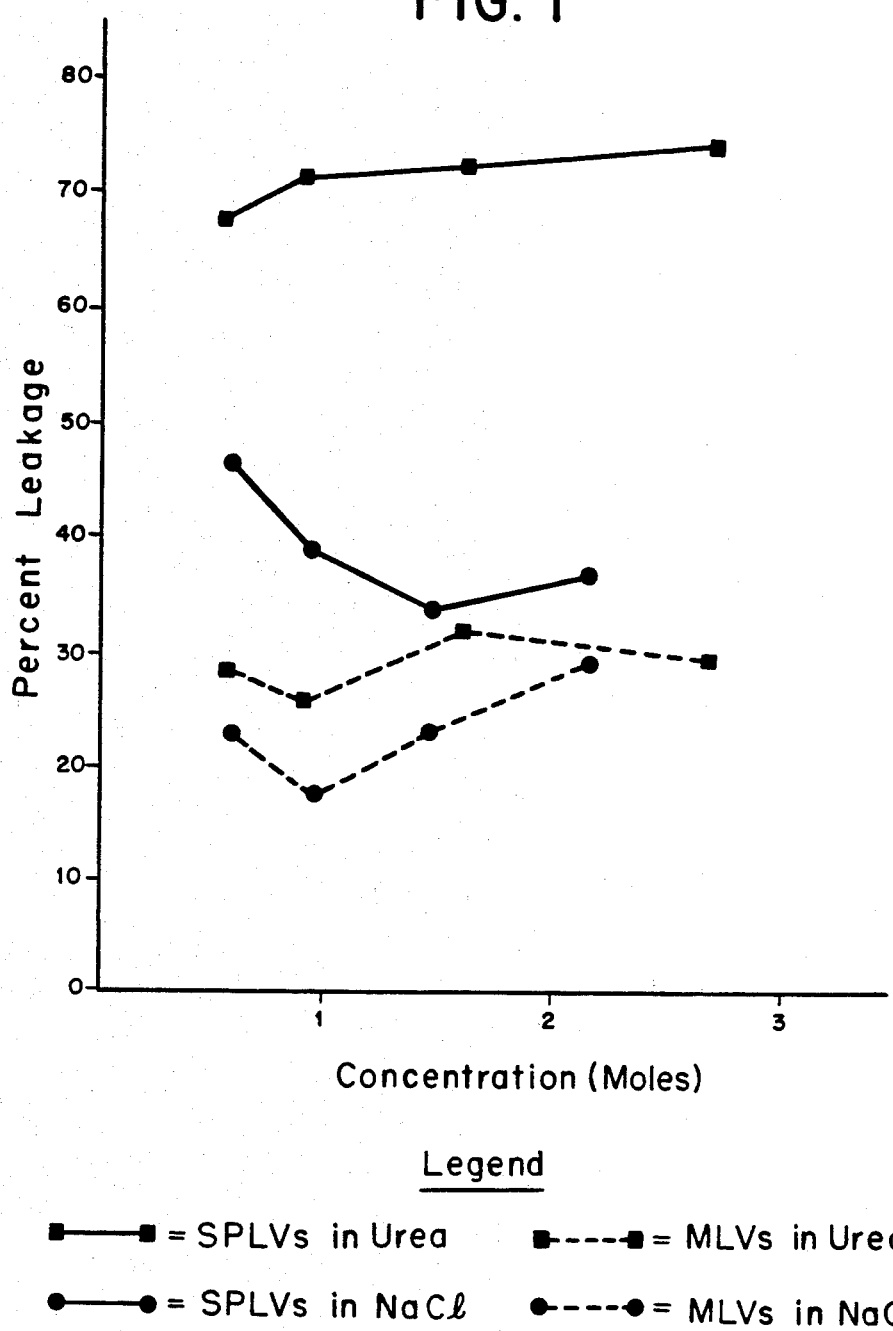

United States Patent [19]

Lenk et al.

[11] Patent Number: 4,522,803
[45] Date of Patent: Jun. 11, 1985

[54] STABLE PLURILAMELLAR VESICLES, THEIR PREPARATION AND USE

[75] Inventors: Robert P. Lenk, Lambertville; Michael W. Fountain, Plainsboro; Andrew S. Janoff, Lawrenceville; Marc J. Ostro, North Brunswick; Micrea C. Popescu, Plainsboro, all of N.J.

[73] Assignee: The Liposome Company, Inc., Princeton, N.J.

[21] Appl. No.: 476,496

[22] Filed: Mar. 24, 1983

Related U.S. Application Data

[63] Continuation-in-part of Ser. No. 463,900, Feb. 4, 1983, abandoned, Ser. No. 447,247, Dec. 6, 1982, abandoned, Ser. No. 411,466, Aug. 25, 1982, abandoned, Ser. No. 362,995, Mar. 29, 1982, abandoned, Ser. No. 362,994, Mar. 29, 1982, abandoned.

[51] Int. Cl.$^3$ .......................... A61J 3/07; A61K 9/52; A61K 43/00; B01J 13/02
[52] U.S. Cl. ................................. 424/1.1; 71/DIG. 1; 424/7.1; 424/19; 424/38; 264/4.6; 428/402.2; 436/829
[58] Field of Search ...................... 428/402.2; 264/4.6; 424/1.1, 7.1, 19, 38; 436/829

[56] References Cited

U.S. PATENT DOCUMENTS

| | | | |
|---|---|---|---|
| 4,115,544 | 9/1978 | Shell | 424/19 X |
| 4,224,179 | 9/1980 | Schneider | 264/4.6 X |
| 4,235,871 | 11/1980 | Papahadjopoulos et al. | 424/38 X |

OTHER PUBLICATIONS

Olitzki: "Immunological Methods in Brucellosis Research, Part II: In Vivo Procedures", S. Karger, Basel (Switzerland), 1970, pp. 196–203.
Gregoriadis: "The Carrier Potential of Liposomes . . . , The New England Journal of Medicine", vol. 295, No. 13, Sep. 23, 1976, pp. 704–710.
Cecil Textbook of Medicine, 15th Edition, Edited by Beeson et al., W. B. Saunders Co., Philadelphia, 1979, pp. 396–399, 475–479 and 817–821.
Bangham et al., 1965, J. Mol. Biol. 13:238–252.
Deamer and Bangham, 1976, Biochim. Biophys. Acta 443:629–634.
Lenk et al., 1982, Eur. J. Biochem. 121:475–482.
Papahadjopoulos and Miller, 1967, Biochim. Biophys. Acta 135:624–638.
Schwendener et al., 1981, Biochem. Biophys. Res. Commun. 100:1055–1062.
Szoka and Papahadjopoulos, 1978, Proc. Nat'l. Acad. Sci. USA 75:4194–4198.

*Primary Examiner*—Richard D. Lovering
*Attorney, Agent, or Firm*—Pennie & Edmonds

[57] ABSTRACT

A new and substantially improved type of lipid vesicle, called stable plurilamellar vesicles (SPLVs), are described, as well as the process for making the same. SPLVs are stable during storage and can be used in vivo for the sustained release of compounds and in the treatment of disease.

44 Claims, 7 Drawing Figures

Legend
■——■ = SPLVs in Urea     ■----■ = MLVs in Urea
●——● = SPLVs in NaCℓ     ●----● = MLVs in NaCℓ

Electron Spin Resonance Spectra

FIG. 5

Surviving Brucella canis in Spleens of Mice after Two-Stage Treatment with Streptomycin

[Bar chart: Y-axis "Brucella canis Recovered per Organ" on log scale from 0 to $10^7$; X-axis "MG/KG" with values 0, 1, 5, 10. At 0: bars A (~$2 \times 10^6$) and B (~$10^6$). At 1: bars C (~$10^6$) and D (~$10^4$). At 5: bars C (~$10^5$) and D (~$2 \times 10^3$). At 10: bar C (~$7 \times 10^4$) and bar D (near 0).]

Legend

A: Control    B: Buffer-Filled SPLVs
C: Streptomycin
D: SPLV-Entrapped Streptomycin

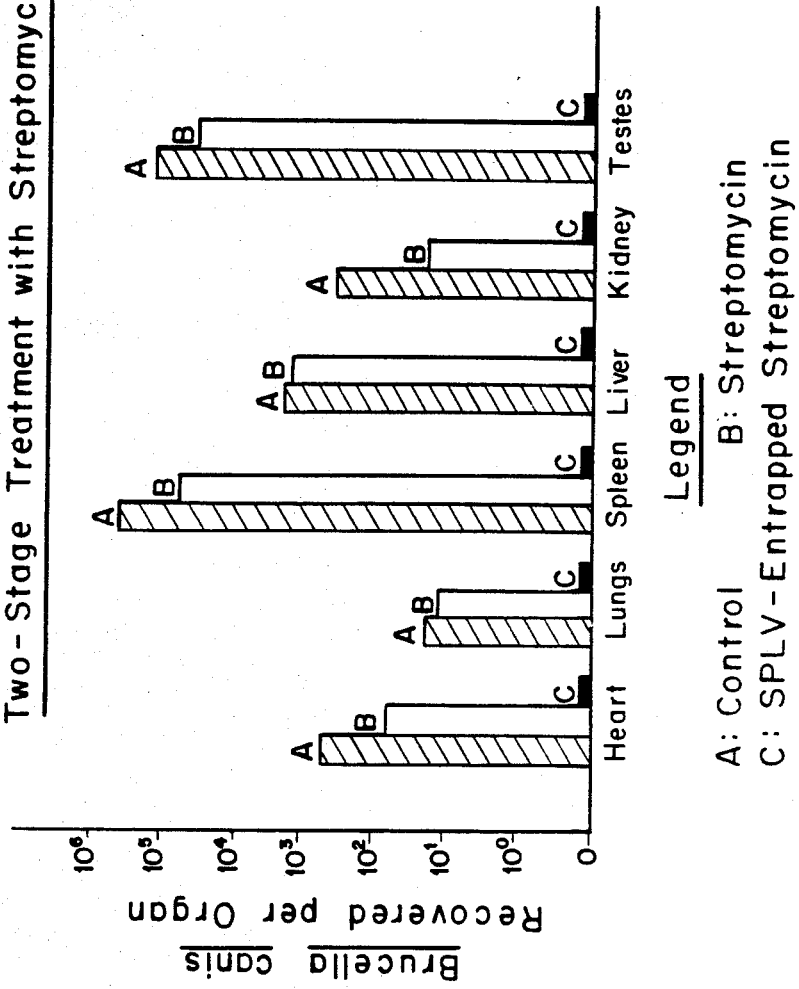

FIG. 7

Surviving Brucella abortus in Spleens of Guinea Pigs after Two-Stage Treatment with Streptomycin

STABLE PLURILAMELLAR VESICLES, THEIR PREPARATION AND USE

The present application is a continuation-in-part of applicant's prior copending applications Ser. No. 463,900 by M. W. Fountain and R. P. Lenk filed Feb. 4, 1983, and now abandoned; Ser. No. 447,247 by R. P. Lenk, M. W. Fountain, A. S. Janoff, filed Dec. 6, 1982, and now abandoned; Ser. No. 411,466 by M. W. Fountain, M. J. Ostro, M. Popescu, and R. P. Lenk, filed Aug. 25, 1982, and now abandoned; Ser. No. 362,995 by M. W. Fountain filed Mar. 29, 1982, and now abandoned; Ser. No. 362,994 by M. W. Fountain filed Mar. 29, 1982, and now abandoned which are herein incorporated by reference.

TABLE OF CONTENTS

1. Field of the Invention
2. Background of the Invention
   2.1. Liposomes
   2.2. Uses of Liposomes
3. Summary of the Invention
4. Brief Description of the Figures
5. Detailed Description of the Invention
   5.1. Preparation of SPLVs
   5.2. Characterization of SPLVs
      5.2.1. Stability of SPLVs in Storage
      5.2.2. Stability of SPLVs in Other Environments
      5.2.3. Characteristics of SPLVs Administered In Vivo
      5.2.4. Electron Spin Resonance
      5.2.5. Entrapment of Active Material by SPLVs
      5.2.6. Interaction of SPLV with Cells
      5.2.7. Buoyant Density of SPLVs
      5.2.8. Volume of SPLVs
      5.2.9. Osmotic Properties of SPLVs
   5.3. Uses of SPLVs
      5.3.1. Delivery of Bioactive Compounds
      5.3.2. Treatment of Pathologies
6. Example: Preparation of SPLVs
   6.1. SPLVs Containing Antibiotics
   6.2. SPLVs Containing Other Membrane Constituents
   6.3. SPLVs Containing Pilocarpine
   6.4. SPLVs Prepared with and without BHT
7. Example: SPLV Mediated Delivery In Vitro
8. Example: Treatment of Intracellular Infections
   8.1. Effect of a Single Treatment of *B. Canis* Infection Using SPLV-Entrapped Antibiotic
   8.2. Effect of Multiple Treatment of *B. Canis* Infection Using SPLV-Entrapped Antibiotic
   8.3. Effectiveness of Treatments Using MLVs as Compared to SPLVs
   8.4. Effect of Various SPLV-entrapped Antibiotics on Treatment of Infection
   8.5. Treatment of Dogs Infected with *B. Canis*
   8.6. Treatment of *B. Abortus* in Guinea Pigs
   8.7. Treatment of *B. Abortus* Infection in Cows
9. Example: Treatment of Ocular Afflictions
   9.1. Treatment of Infectious Keratoconjunctivitis in Mice
   9.2. Treatment of Rabbit Conjunctiva Using SPLV-Entrapped Antibiotic
   9.3. Treatment of Keratoconjunctivitis Resulting from Subcutaneous Infections
   9.4. Evaluation of the Effectiveness of SPLVs as Compared to Liposome Preparations in the Treatment of Ocular Infections
10. Example: Treatment of Viral Infections
    10.1 Treatment of Lethal Lymphocytic Choriomeningitis Virus Infections in Mice

1. FIELD OF THE INVENTION

This invention relates to liposomes and their uses as carriers in delivery systems. More specifically, it relates to a new type of lipid vesicle having unique properties which confer special advantages such as increased stability and high entrapment efficiency.

The compositions and methods described herein have a wide range of applicability to fields such as carrier systems and targeted delivery systems. The practice of the present invention is demonstrated herein by way of example for the treatment of brucellosis, the treatment of ocular infections, and the treatment of lymphocytic meningitis virus infections.

2. BACKGROUND OF THE INVENTION

2.1. Liposomes

Liposomes are completely closed bilayer membranes containing an entrapped aqueous phase. Liposomes may be any variety of unilamellar vesicles (possessing a single membrane bilayer) or multilamellar vesicles (onion-like structures characterized by concentric membrane bilayers each separated from the next by a layer of water).

The original liposome preparations of Bangham et al. (1965, J. Mol. Biol. 13:238–252) involved suspending phospholipids in an organic solvent which was then evaporated to dryness leaving a waxy deposit of phospholipid on the reaction vessel. Then an appropriate amount of aqueous phase was added, the mixture was allowed to "swell", and the resulting liposomes which consisted of multilamellar vesicles (hereinafter referred to as MLVs) were dispersed by mechanical means. The structure of the resulting membrane bilayer is such that the hydrophobic (non-polar) "tails" of the lipid orient toward the center of the bilayer while the hydrophilic (polar) "heads" orient towards the aqueous phase. This technique provided the basis for the development of the small sonicated unilamellar vesicles (hereinafter referred to as SUVs) described by Papahadjapoulos and Miller (1967, Biochim. Biophys. Acta. 135:624–638). These "classical liposomes", however, had a number of drawbacks not the least of which was a low volume of entrapped aqueous space per mole of lipid and a restricted ability to encapsulate large macromolecules.

Efforts to increase the entrapped volume involved first forming inverse micelles or liposome precursors, i.e., vesicles containing an aqueous phase surrounded by a monolayer of lipid molecules oriented so that the polar head groups are directed towards the aqueous phase. Liposome precursors are formed by adding the aqueous solution to be entrapped to a solution of polar lipid in an organic solvent and sonicating. The liposome precursors are then evaporated in the presence of excess lipid. The resultant liposomes, consisting of an aqueous phase entrapped by a lipid bilayer are dispersed in aqueous phase (see U.S. Pat. No. 4,224,179 issued Sept. 23, 1980 to M. Schneider).

In another attempt to maximize the efficiency of entrapment Papahadjopoulos (U.S. Pat. No. 4,235,871 issued Nov. 25, 1980) describes a "reverse-phase evaporation process" for making oligolamellar lipid vesicles also known as reverse-phase evaporation vesicles (hereinafter referred to as REVs). According to this procedure, the aqueous material to be entrapped is added to a mixture of polar lipid in an organic solvent. Then a homogeneous water-in-oil type of emulsion is formed and the organic solvent is evaporated until a gel is formed. The gel is then converted to a suspension by dispersing the gel-like mixture in an aqueous media. The REVs produced consist mostly of unilamellar vesicles and some oligolamellar vesicles which are characterized by only a few concentric bilayers with a large internal aqueous space. Certain permeability properties of REVs were reported to be similar to those of MLVs and SUVs (see Szoka and Papahadjopoulos, 1978, Proc. Natl. Acad. Sci. U.S.A. 75:4194–4198).

Liposomes which entrap a variety of compounds can be prepared, however, stability of the liposomes during storage is invariably limited. This loss in stability results in leakage of the entrapped compound from the liposomes into the surrounding media, and can also result in contamination of the liposome contents by permeation of materials from the surrounding media into the liposome itself. As a result the storage life of traditional liposomes is very limited. Attempts to improve stability involved incorporating into the liposome membrane certain substances (hereinafter called "stabilizers") which affect the physical properties of the lipid bilayers (e.g., steroid groups). However, many of these substances are relatively expensive and the production of such liposomes is not cost-effective.

In addition to the storage problems of traditional liposomes a number of compounds cannot be incorporated into these vesicles. MLVs can only be prepared under conditions above the phase-transition temperature of the lipid membrane. This precludes the incorporation of heat labile molecules within liposomes that are composed of phospholipids which exhibit desirable properties but possess long and highly saturated side chains.

2.2. Uses of Liposomes

Application of liposomes to therapeutic uses is described in *Liposomes: From Physical Structures To Therapeutic Applications,* Knight, ed. Elsevier, North-Holland Biomedical Press, 1981. Much has been written regarding the possibilities of using these membrane vesicles for drug delivery systems though a number of problems with such systems remain. See, for example, the disclosures in U.S. Pat. No. 3,993,754 issued on Nov. 23, 1976, to Yneh-Erh Rahman and Elizabeth A. Cerny, and U.S. Pat. No. 4,145,410 issued on Mar. 20, 1979, to Barry D. Sears. In a liposome drug delivery system the medicament is entrapped during liposome formation and then administered to the patient to be treated. The medicament may be soluble in water or in a non-polar solvent. Typical of such disclosures are U.S. Pat. No. 4,235,871 issued Nov. 25, 1980, to Papahadjopoulos and Szoka and U.S. Pat. No. 4,224,179, issued Sept. 23, 1980 to M. Schneider.

Some desirable features of drug delivery systems are resistance to rapid clearance of the drug accompanied by a sustained release of the drug which will prolong the drug's action. This increases effectiveness of the drug and allows the use of fewer administrations. Some of the problems encountered in using liposome preparations in vivo include the following: (1) Liposome entrapped materials leak when the liposomes are incubated in body fluids. This has been attributed to the removal of the liposomal phospholipids by plasma high density lipoproteins (HDL), or to the degradation of the liposome membrane by phospholipases, among other reasons. A result of the degradation of the liposomes in vivo is that almost all the liposomal contents are released in a short period of time, therefore, sustained release and resistance of the drug to clearance are not achieved. (2) On the other hand, if a very stable liposome is used in vivo (i.e., liposomes which do not leak when incubated in body fluids), then the liposomal contents will not be released as needed. As a result, these stable liposomes are ineffective as carriers of therapeutic substances in vivo because the sustained release or the ability to release the liposomal contents when necessary is not accomplished. However, if one is treating an intracellular infection, the maintenance of stability in biological fluids until the point that the liposome is internalized by the infected cell, is critical. (3) The cost-effectiveness of the liposome carriers used in delivery systems. For example, an improved method for the chemotherapy of leishmanial infections using liposome encapsulated anti-leishmanial drug has been reported by Steck and Alving in U.S. Pat. No. 4,186,183 issued on Jan. 29, 1980. The liposomes used in the chemotherapy contained a number of stabilizers which increased the stability of the liposomes in vivo. However, as previously mentioned, these stabilizers are expensive and the production of liposomes containing these stabilizers is not cost-effective. (4) Ultimately, the problem encountered in the use of liposomes as carriers in drug delivery systems is the inability to effect a cure of the disease being treated. In addition to the inability to resist rapid clearance and to effect sustained release, a number of other explanations for the inability to cure diseases are possible. For instance, if the liposomes are internalized into target cells or phagocytic cells (e.g., reticuloendothelial cells), they are cleared from the system rapidly, rendering the entrapped drug largely ineffective against diseases of involving cells other than the RES. After phagocytosis, the liposomal contents are packaged within lysosomes of the phagocytic cell. Very often the degradative enzymes contained within the lysosome will degrade the entrapped compound or render the compound inactive by altering its structure or cleaving the compound at its active site. Furthermore, the liposomes may not deliver a dose which is effective due to the low efficiency of entrapment of active compound into the vesicles when prepared.

Liposomes have also been used by researchers as model membrane systems and have been employed as the "target cell" in complement mediated immunoassays. However, when used in such assays, it is important that the liposome membrane does not leak when incubated in sera because these assays measure the release of the liposome contents as a function of serum complement activation by immune complex formation involving certain immunoglobulin classes (e.g., IgM and certain IgG molecules).

3. SUMMARY OF THE INVENTION

This invention presents a new and substantially improved type of lipid vesicles which hereinafter will be referred to as stable plurilamellar vesicles (SPLVs). Aside from being structurally different than multilamellar vesicles (MLVs), SPLVs are also prepared differently than MLVs, possess unique properties when compared to MLVs, and present a variety of different advantages when compared to such MLVs. As a result of these differences, SPLVs overcome many of the problems presented by conventional lipid vesicles heretofore available.

A heterogeneous mixture of lipid vesicles is realized when SPLVs are synthesized. Evidence indicates that the lipids in the SPLVs are organized in a novel supramolecular structure. Many of the lipid vesicles possess a high number of bilayers, occasionally as high as one hundred layers. It may be possible that this high degree of layering contributes to many of the surprising properties possessed by SPLVs, although the explanations are theoretical.

The properties of SPLVs include: (1) the ability to cure certain diseases which other methodologies cannot cure; (2) greatly increased stability of the SPLVs during storage in buffer; (3) the increased ability of SPLVs to withstand harsh physiologic environments; (4) the entrapment of materials at a high efficiency; (5) the ability to stick to tissues and cells for prolonged periods of time; (6) the ability to release of entrapped materials slowly in body fluids; (7) the delivery and ultimate dispersal of the liposomal contents throughout the cytosol of the target cell; (8) improved cost-effectiveness in preparation; and (9) release of compounds in their bioactive forms in vivo.

Due to the unique properties of SPLVs they are particularly useful as carriers in delivery systems in vivo because they are resistant to clearance and are capable of sustained release. Methods for the use of SPLVs for the delivery of bioactive compounds in vivo and the treatment of pathologies, such as infections, are described.

4. BRIEF DESCRIPTION OF THE FIGURES

FIG. 1 graphically demonstrates the difference in membrane stability (as reflected by % leakage) between MLVs and SPLVs treated with varying concentrations of urea.

Figure 2:
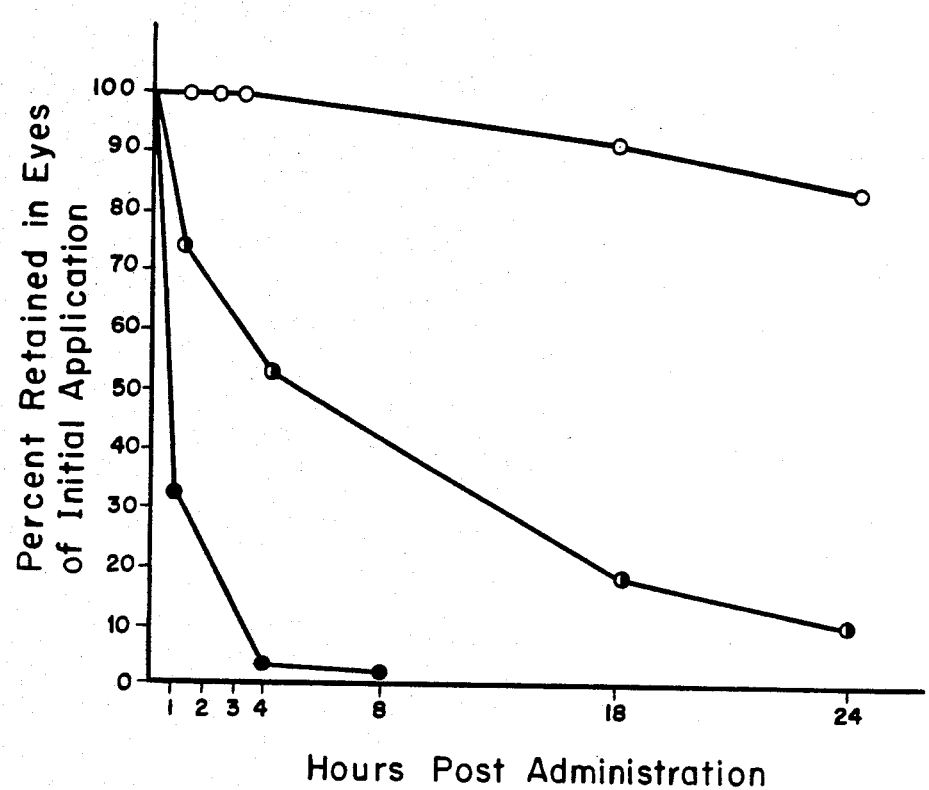

FIG. 2 graphically represents the retention of both the lipid and aqueous phases of SPLVs in eyelid tissues of mice, and the sustained release of gentamycin from the SPLVs in vivo.

Figure 3:
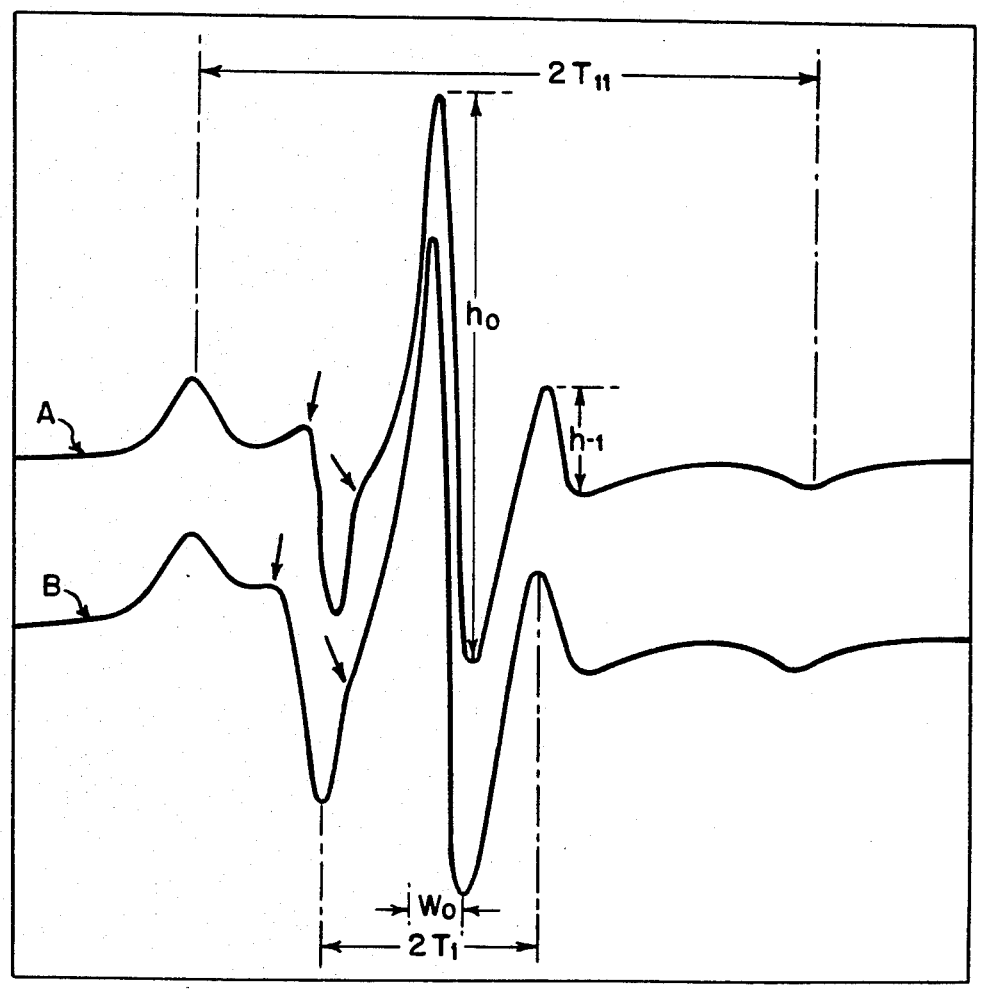

FIG. 3 represents the electron spin resonance absorption spectrum of SPLVs (A) compared to that of MLVs (B).

Figure 4:
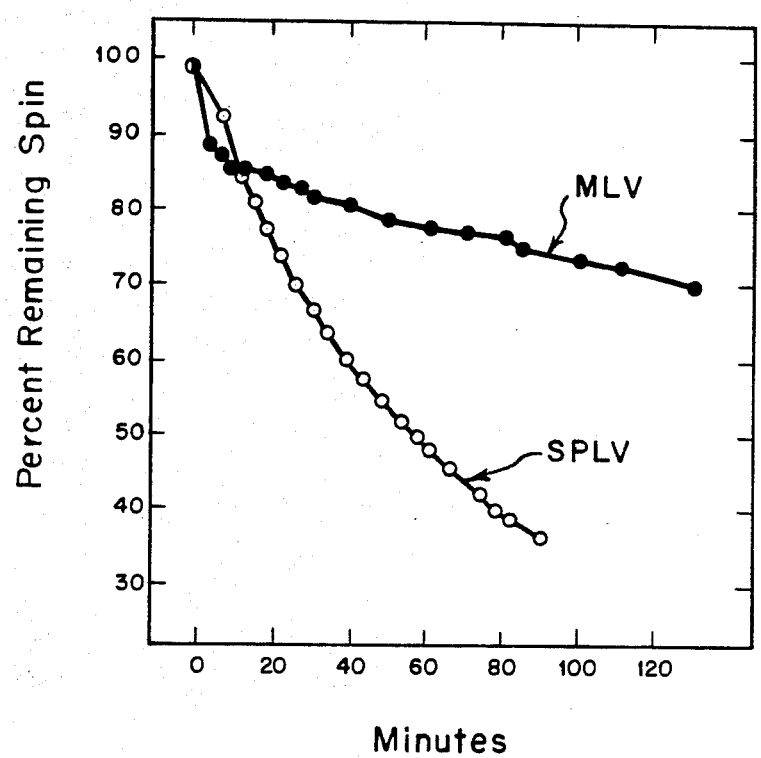

FIG. 4 graphically demonstrates the difference in the ability of ascorbate to reduce doxyl spin probes in SPLVs and in MLVs.

FIG. 5 graphically represents the effectiveness of a two stage treatment of *Brucella canis* infections in mice using SPLV-entrapped streptomycin based on *B. canis* recoverable from spleens of infected mice.

FIG. 6 graphically represents the effectiveness of a two stage treatment of *B. canis* infections in mice using SPLV-entrapped streptomycin based on *B. canis* recoverable from organs of infected mice.

FIG. 7 graphically represents the effectiveness of a two stage treatment of *Brucella abortus* in guinea pigs using SPLV-entrapped streptomycin.

5. DETAILED DESCRIPTION OF THE INVENTION

5.1. Preparation of SPLVs

SPLVs are prepared by a process which results in a product unique from any other liposome previously described.

SPLVs are lipid vesicles possessing from a few to over one hundred lipid bilayers. The membrane bilayer is composed of a bimolecular layer of an amphipathic lipid in which the non-polar hydrophobic hydrocarbon "tails" point inward towards the center of the bilayer and the polar, hydrophilic "heads" point towards the aqueous phase. Occluded by the bilayers is an aqueous compartment, part of wich makes up the lumen of the vesicle, and part of which lies between adjacent layers. Complexed with the lipid bilayers can be a variety of proteins, glycoproteins, glycolipids, mucopolysaccharides, and any other hydrophobic and/or amphipathic substance.

SPLVs are prepared as follows: An amphipathic lipid or mixture of lipids is dissolved in an organic solvent. Many organic solvents are suitable, but diethyl ether, fluorinated hydrocarbons and mixtures of fluorinated hydrocarbons and ether are preferred. To this solution are added an aqueous phase and the active ingredient to be entrapped. This biphasic mixture is converted to SPLVs by emulsifying the aqueous material within the solvent while evaporating the solvent. Evaporation can be accomplished during sonication by any evaporative technique, e.g., evaporation by passing a stream of inert gas over the mixture, by heating, or by vacuum. The volume of solvent used must exceed the aqueous volume by a sufficient amount so that the aqueous material can be completely emulsified in the mixture. In practice, a minimum of roughly 3 volumes of solvent to 1 volume of aqueous phase may be used. In fact the ratio of solvent to aqueous phase can vary to up to 100 or more volumes of solvent to 1 volume aqueous phase. The amount of lipid must be sufficient so as to exceed that amount needed to coat the emulsion droplets (about 40 mg of lipid per ml of aqueous phase). The upper boundary is limited only by the practicality of cost-effectiveness, but SPLVs can be made with 15 gm of lipid per ml of aqueous phase.

The process produces lipid vesicles with different supermolecular organization than conventional liposomes. According to the present invention, the entire process can be performed at a temperature range of 4°–60° C. regardless of the phase transition temperature of the lipid used. The advantage of this latter point is that heat labile products which have desirable properties, for example, easily denatured proteins, can be incorporated in SPLVs prepared from phospholipid such as distearoylphosphatidylcholine, but can be formed into conventional liposomes only at temperatures above their phase-transition-temperature. The process usually allows more than 20% of the available water soluble material to be encapsulated and more than 40% of the available lipid soluble material to be encapsulated. With MLVs the entrapment of aqueous phase usually does not exceed 10%.

Most amphipathic lipids may be constituents of SPLVs. Suitable hydrophilic groups include but are not limited to: phosphato, carboxylic, sulphato and amino groups. Suitable hydrophobic groups include but are not limited to: saturated and unsaturated aliphatic hydrocarbon groups and aliphatic hydrocarbon groups substituted by at least one aromatic and/or cycloaliphatic group. The preferred amphipathic compounds are phospholipids and closely related chemical structures. Examples of these include but are not limited to: lecithin, phosphatidylethonolamine, lysolecithin, lysophatidylethanolamine, phosphatidylserine, phosphatidylinositol, sphingomyelin, cardiolipin, phosphatidic acid and the cerebrosides. Specific examples of suitable lipids useful in the production of SPLVs are phospholipids which include the natural lecithins (e.g., egg lecithin or soybean lecithin) and synthetic lecithins, such as saturated synthetic lecithins (e.g., dimyristoylphosphatidylcholine, or dipalmitoyl-phosphatidylcholine or distearoylphosphatidylcholine) and unsaturated synthetic lecithins (e.g., dioloyl-phosphatidylcholine or dilinoloylphosphatidylcholine. The SPLV bilayers can contain a steroid component such as cholesterol, coprostanol, cholestanol, cholestane and the like. When using compounds with acidic hydrophilic groups (phosphato, sulfato, etc.) the obtained SPLVs will be anionic; with basic groups such as amino, cationic liposomes will be obtained; and with polyethylenoxy or glycol groups neutral liposomes will be obtained. The size of the SPLVs varies widely. The range extends from about 100 nm to about 10,000 nm (10 microns) and usually about 100 nm to about 1,500 nm.

Virtually any bioactive compound can be entrapped within a SPLV (entrapped is defined as entrapment within the aqueous compartment or within the membrane bilayer). Such compounds include but are not limited to nucleic acids, polynucleotides, antibacterial compounds, antiviral compounds, antifungal compounds, anti-parasitic compounds, tumoricidal compounds, proteins, toxins, enzymes, hormones, neurotransmitters, glycoproteins, immunoglobulins, immunomodulators, dyes, radiolabels, radio-opaque compounds, fluorescent compounds, polysaccharides, cell receptor binding molecules, anti-inflammatories, antiglaucomic agents, mydriatic compounds, local anesthetics, etc.

The following is an example of the proportions that may be used in SPLV synthesis: SPLVs may be formed by adding 50 micromoles of phospholipid to 5 ml of diethyl ether containing 5 micrograms of BHT (butylatedhydroxytoluene) and then adding 0.3 ml of aqueous phase containing the active substance to be encapsulated. The resultant solution which comprises the material to be entrapped and the entrapping lipid is sonicated while streaming an inert gas over the mixture thus removing most of the solvent. This embodiment produces particularly stable SPLVs partially because of the incorporation of BHT into the vesicles.

See also Lenk, et al., 1982, Eur. J. Biochem. 121:475–482 which describes a process for making liposome-encapsulated antibodies by sonicating and evaporating a solution of cholesterol and phosphatidylcholine in a mixture of chloroform and ether with aqueous phase added, but does not set forth the relative proportions of lipid to aqueous phase.

5.2. Characterization of SPLVs

SPLVs are clearly distinct in their properties from liposomes with a single or several lamellae (e.g., SUVs, and REVs). Freeze-fracture electron microscopy indicates that SPLV preparations are substantially free of SUVs and REVs, that is, less than 20% of the vesicles are unilamellar. They are, however, indistinguishable from MLVs by electron microscopic techniques although many of their physical properties are different. Thus, the following detailed comparison is focused on distinguishing SPLVs from MLVs.

5.2.1. Stability of SPLVs in Storage

Stability of a lipid vesicle refers to the ability of the vesicle to sequester its occluded space from the external environment over a long period of time. For a lipid vesicle to be useful it is paramount that it be stable in storage and handling. For some applications, however, it is desirable that the vesicle leak its contents slowly when applied. For other applications it is desirable that the vesicle remain intact after administration until it reaches its desired site of action. It will be seen that SPLVs demonstrate these desirable characteristics, while MLVs do not.

There are two factors that cause vesicles to leak. One is auto-oxidation of the lipids whereby the hydrocarbon chains form peroxides which destabilize the bilayers. This oxidation can be drastically slowed down by the addition of antioxidants such as butylated hydroxy toluene (BHT) to the vesicle preparation. Vesicles can also leak because agents in the exterior environment disrupt the bilayer organization of the lipids such that the lipids remain intact, but the membrane develops a pore.

Preparations of lipid vesicles are white in color when first made. Upon auto-oxidation, the preparation becomes discolored (brownish). A comparison of MLVs to SPLVs prepared using the same lipid and aqueous components reveals that MLVs discolor within one to two weeks whereas SPLVs remain white for at least two months. This is supported by thin layer chromatography of the constituent lipids which showed degradation of the lipids in the MLVs but not of the lipids of the SPLVs. When these vesicles are prepared by adding BHT as well as the other constituents, then MLVs appear slightly discolored within one month whereas the SPLVs remain white and appear stable for at least 6 months and longer.

When placed in a buffer containing isotonic saline at neutral pH, SPLVs containing antibiotic are stable for more than four months, as demonstrated in Table I. These data indicate that none of the antibiotic originally encapsulated within the SPLVs leaked out in the period of the experiment.

Other evidence indicates that SPLVs are able to sequester an encapsulated agent from molecules as small as calcium ions for more than six months. Arsenazo III is a dye which changes color from red to blue with the slightest amount of divalent cation present. By encapsulating the dye in SPLVs and adding calcium chloride to the storage buffer it is possible to measure the stability of the vesicles by looking for a color change. The color remains undetectably different from its original color for at least 6.5 months, demonstrating that neither has the dye leaked out nor the ion leaked in.

TABLE I

| STABILITY OF EGG PHOSPHATIDYLCHOLINE SPLVs AFTER STORAGE IN SEALED CONTAINERS AT 4° C. FOR 4½ MONTHS[a] | | | |
| --- | --- | --- | --- |
| Entrapped Drug | Initial Entrapment % | Leakage Into Supernatant[b] | Bioavailability of Entrapped Drug (%) |
| Streptomycin Sulfate | 34.1 | 0 | 97 |
| Spectinomycin | 37.2 | 0 | 84 |
| Chloramphenicol | 35.2 | 0 | 89 |

TABLE I-continued
STABILITY OF EGG PHOSPHATIDYLCHOLINE SPLVs AFTER STORAGE IN SEALED CONTAINERS AT 4° C. FOR 4½ MONTHS[a]

| Entrapped Drug | Initial Entrapment % | Leakage Into Supernatant[b] | Bioavailability of Entrapped Drug (%) |
|---|---|---|---|
| Oxytetracycline | 18.8 | 0 | 91 |
| Erythromycin | 0.4 | 0 | 97 |
| Sulfamerazine | 6.3 | 0 | 93 |

[a]SPLVs were prepared using 127 μM egg phosphatidylcholine (EPC) and 25 μM drug. At the end of 4½ months storage at 4° C. the SPLVs were separated from storage buffer by centrifugation. Serial dilutions of the SPLV contents and the supernatant were applied to bacterial lawns in order to determine bioactivity as compared to standard dilutions of antibiotic.
[b]0 indicates below detectable levels These experiments demonstrate that SPLVs are sufficiently stable to withstand storage and handling problems. Although it is possible to make MLVs which are stable for this long, they must be made from synthetic lipids such as DSPC and thus become prohibitively expensive.

5.2.2. Stability of SPLVs in Other Environments

Placing lipid vesicles in a medium which contains membrane perturbing agents is a way to probe different molecular organizations. Depending on how the membrane is organized, different vesicles will respond differently to such agents.

In the following experiments vesicles were prepared which contained a radioactive tracer molecule ($^3$H inulin) within the occluded aqueous compartment. Inulin, a polysaccharide, partitions into the aqueous phase, and thus when radiolabeled may be used to trace the aqueous contents of lipid vesicles. After an appropriate interval of exposure to a given agent, the vesicles were separated from the medium by centrifugation, and the relative amount of radioactivity that escaped from the vesicles into the medium was determined. These results are reported in Table II; values are expressed as percent leaked, meaning the proportion of radioactive material in the surrounding medium relative to the starting amount encapsulated in the vesicles.

SPLVs are more stable than MLVs in hydrochloric acid. Table II illustrates that both MLVs and SPLVs, when made from egg lecithin, are destabilized when exposed to 0.125 N hydrochloric acid for one hour. However, it is noteworthy that the SPLVs are considerably less susceptible to the acid than MLVs. Presumably this different response reflects an intrinsic difference in the way the lipids interact with their environment.

TABLE II
STABILITY OF SPLVS IN OTHER ENVIRONMENTS

| Incubating Medium[a] | % LEAKAGE | |
|---|---|---|
| | MLVs | SPLVs |
| Hydrochloric Acid | | |
| 0.125 M | 90.5 | 55.2 |
| Urea | | |
| 1 M | 21.7 | 44.8 |
| Guanidine | | |
| 0.5 M | 5.7 | 7.4 |
| 1.0 M | 8.3 | 10.1 |
| Ammonium Acetate | | |
| 0.5 M | 27.0 | 67.0 |
| 1.0 M | 25.9 | 54.7-63.1 |
| Serum | 76.2 | 57.8 |

[a]Incubation time is 2 to 4 hours except incubation in HCl was for 1 hour.

SPLVs also respond differently than MLVs when exposed to urea (FIG. 1 and Table II). Urea is a molecule with both a chaotropic effect (disrupts the structure of water) and a strong dipole moment. It is observed that SPLVs are far more susceptible to urea than they are to an osmotic agent such as sodium chloride at the same concentration (FIG. 1). MLVs do not leak significantly more in urea than they would in sodium chloride. Although the explanations for this different behavior are theoretical, it would appear that the response is due to the dipole effect, rather than a chaotropic property, since guanidine, a molecule similiar to urea, does not destabilize SPLVs (Table II). Although guanidine is also strongly chaotropic, it does not possess a strong dipole moment.

SPLVs are also susceptible to ammonium acetate, while MLVs are not (Table II). However, neither ammonium ion (in ammonium chloride) nor acetate (in sodium acetate) are particularly effective in causing SPLVs to destabilize. Thus it would appear that it is not the ion itself, but the polarity of the ammonium acetate which is responsible for inducing leakage.

Initially these results seem surprising because SPLVs are much more stable than MLVs when incubated in body fluids such as sera or blood. However a theoretical explanation for these results can be proposed (of course other explanations are possible). If the stability of the SPLV is due to the unique structure of its membrane bilayers such that the polar groups of the membrane lipids are hydrated by a cloud of oriented water molecules, or hydration shell, then it is possible that any agent which disrupts or interferes with such hydration shells would promote changes in structural membrane integrity, and therefore, leakage.

Independent of the theoretical explanations for the destabilization of SPLVs in urea, the results serve to demonstrate characteristic differences between the structure of MLVs and SPLVs. This difference serves a very useful purpose in application. As described infra, SPLVs become slowly leaky when applied to the eye. Presumably this desired slow release of contents is due to a similar destabilization of the SPLVs when exposed to tear fluid.

SPLVs are more stable in serum than MLVs. Many applications of lipid vesicles include administering them intraperitoneally, such as for the treatment of brucellosis. To be effective, the vesicles must survive for a sufficient time to reach their desired target. SPLVs and MLVs, both made from egg lecithin, were exposed to fetal bovine serum which contained active complement, (Table II). After 48 hours exposure at 37° C., SPLVs are demonstrably more stable than MLVs.

5.2.3. Characteristics of SPLVs Administered in Vivo

SPLVs demonstrate a number of characteristics which make them particularly suitable as carriers for delivery systems in vivo:

(A) SPLVs are resistant to clearance. When SPLVs are administered to an organism both the lipid component and the entrapped active ingredient are retained in the tissues and by the cells to which they are administered;

(B) SPLVs can be engineered to provide sustained release. The stability of SPLVs is "adjustable" in that SPLVs are very stable during storage and are stable in the presence of body fluids but when administered in vivo a slow leakage of the active ingredient permits the sustained release of the active ingredient;

(C) Because of the high level of entrapment and stability when administered, effective doses of the active ingredient are released; and (D) The production of SPLVs is very cost effective in that stability of the vesicles is achieved without incorporating expensive stabilizers into the bilayers.

The following experiments demonstrate some of these characteristics of SPLVs when administered topically onto the eyes of test animals. The SPLVs used in these experiments were prepared as previously described except that the lipid bilayer and the active ingredient were each radiolabeled in order to trace these components in the eye tissues over a period of time.

SPLVs were prepared using 100 mg egg phosphatidylcholine (EPC) and 100 mg gentamycin sulfate. The lipid component was radiolabeled by the incorporation of trace amounts of $^{125}$I-phosphatidylethanolamine ($^{125}$I-PE) into the bilayers, whereas the active ingredient in the aqueous phase was radiolabeled by the addition of $^{125}$I-gentamycin sulfate ($^{125}$I-GS). The SPLVs were washed with buffer repeatedly in order to effectively remove unincorporated or unencapsulated materials.

An aliquot of the SPLV preparation was removed and extracted in order to separate the organic phase from the aqueous phase. The radioactivity of each phase was measured in order to determine the initial ratio of $^{125}$I-PE:$^{125}$I-GS (cpm (counts per minute) in the lipid phase:cpm in the aqueous phase) which was incorporated into the SPLVs.

The extraction was done as follows: 0.8 ml of 0.4 M NaCl (aqueous), 1 ml chloroform, and 2 ml methanol were mixed to form a homogeneous phase. Then 4 μl of the radiolabeled SPLVs were added and mixed; as the SPLV components dissolved into the organic phase and into the aqueous phase, the mixture, which was initially turbid, became clear. The phases were separated by adding and mixing 1 ml 0.4 M NaCl (aqueous) and 1 ml chloroform, which was then centrifuged at 2,800 × g for 5 minutes. An aliquot (1 ml) of each phase was removed and the radioactivity (in cpm) was measured. (The initial ratio of $^{125}$I-PE:$^{125}$I-GS was 1.55:1).

Fifteen adult female Swiss Webster mice were anesthetized and restrained (in order to prevent them from wiping their eyes). Equal aliquots (2 μl) of the radiolabeled SPLVs in suspension were topically applied to each eye. Groups of three animals were then sacrificed at each of the following points: 1, 2, 3, 18, and 24 hours. Nine female Swiss Webster mice (controls) were treated identically except that equal aliquots (2 μl) of an aqueous solution of radiolabeled gentamycin sulfate were applied topically to each eye. Groups of three control animals were sacrificed at the end of 1, 4, and 8 hours.

Immediately after sacrifice the eyelids of the animals were removed, minced, and extracted (using the procedure previously described) in order to separate the aqueous components from the lipid components. The radioactivity of such phase was determined (as well as the total number of radioactive counts recovered). The radioactivity measured in the lipid phase is an indication of the retention of SPLV lipids by the eye tissue, whereas the radioactivity measured in the aqueous phase is an indication of the retention of gentamycin in the eye tissue. FIG. 2 graphically demonstrates the retention of each component in the eyelid tissue (expressed as the percent of the original number of cpm applied to the eye).

FIG. 2 clearly demonstrates the retention of the SPLV lipid component in the eyelid tissue over a 24 hour period, and the sustained release of gentamycin from the SPLVs over a 24 hour period (as reflected by the percent gentamycin retained in the eyelid tissue during this time). FIG. 2 also demonstrates that unencapsulated gentamycin (aqueous gentamycin administered topically) is rapidly cleared from the eyelid tissue. For example, gentamycin in solution (control) was cleared from the eyelid tissue within 4 hour (less than 5% of the gentamycin remained in the eyelid tissue). On the other hand, more than 50% of the SPLV-encapsulated gentamycin was retained by the eyelid tissue in this 4 hour period; in fact, at the end of 24 hours more than 15% of the SPLV-encapsulated gentamycin was retained by the eyelid tissue. This indicates that approximately 85% of the SPLV-encapsulated gentamycin was released over a 24 hour period whereas 95% of the unencapsulated gentamycin sulfate was cleared within a 4 hour period.

Table III compares the ratio of the SPLV lipid phase::aqueous phase retained in the eyelid tissue at each time point. An increase in this ratio indicates release of gentamycin from the SPLVs.

The bioactivity of the SPLV-encapsulated gentamycin sulfate which was retained by the eyelid tissues was also evaluated. Gentamycin sulfate was recovered from the eyelid tissues by removing an aliquot from the aqueous phase of the eyelid extracts prepared 3 hours after the SPLV-encapsulated gentamycin sulfate was applied to the eye. The aqueous phase was serially diluted and 2 μl aliquots were placed onto *Staphylococcus aureus* lawns on agar plates; after 24 hours incubation the zones of inhibition were measured. The gentamycin sulfate recovered from the eyelid tissue extracts of animals treated with SPLV-encapsulated gentamycin sulfate fully retained its bioactivity.

TABLE III

| | SUSTAINED RELEASE OF SPLV-ENCAPSULATED GENTAMYCIN AFTER TOPICAL APPLICATION IN EYES OF MICE | |
|---|---|---|
| Time Post-Application | Total SPLV Components Recovered from Eyelids (% Initial Dose) | Ratio of SPLV Lipid: Aqueous Phase Retained In Eyelids ($^{125}$I-PE:$^{125}$I-GS) |
| 0 | 100% | 1.55 |
| 1 hr | 100% | 2.1 |
| 3 hr | 100% | 2.82 |
| 18 hr | 94% | 6.89 |
| 24 hr | 85.1% | 7.17 |

5.2.4. Electron Spin Resonance

Although SPLVs and MLVs appear identical by electron microscopy, ESR (electron spin resonance) spectroscopy reveals differences in their supramolecular structure. SPLVs can be distinguished from MLVs on the basis of their molecular architecture as evidence by their increased molecular order, increased molecular motion and greater penetrability to ascorbate. It is likely that these differences in molecular architecture contribute to their different biological effects.

In electron spin resonance spectroscopy a spin probe such as 5-doxyl stearate (5 DS) is incorporated into the lipid bilayer. The unpaired electron of the doxyl group absorbs microwave energy when the sample is inserted into a magnetic field. The spectrum of the absorption allows the determination of three empirical parameters:

S, the order parameter; A·, the hyperfine coupling constant; and Tau the rotational correlation time. A typical reading is shown in FIG. 3, wherein A is the SPLV signal and B is the MLV signal, both are labeled with 5-doxyl stearate. The spectra were taken at room temperature, scan range was 100 Gauss. The order parameter(s) which is dependent on both $2T_1$ and $2T_{11}$ measures the deviation of the observed ESR signal from the case of a completely uniform orientation of the probe. For a uniformly oriented sample S=1.00, a random sample S=0. The hyperfine coupling constant, A·, which can be calculated from $2T_1$ and $2T_{11}$ is considered to reflect local polarity and thus reflects the position of the spin probe within the membrane. The rotational correlation time (which is dependent on $W_o$, $h_o$, h-1) can be thought of as the time required for the molecules to "forget" what their previous spatial orientations were. A typical ESR determination of the differences between SPLVs and MLVs having 5-DS as the spin probe is summarized in Table IV.

Although in both cases the spin probe is reporting from the same depth in the bilayer, SPLVs possess a significantly greater degree of molecular order and molecular motion than MLVs.

Another illustration of the differences between SPLVs and MLVs resides in the ability of ascorbate to reduce doxyl spin probes. It has been known for some time that ascorbate reduces doxyl moieties presumably to their hydroxylamine analogs which do not absorb microwave energy in a magnetic field. In aqueous solutions the reduction occurs rapidly with concomitant loss of ESR signal. If the spin probe is in a protected environment such as a lipid bilayer it may be reduced more slowly or not at all by the hydrophilic ascorbate.

TABLE IV

| ESR CHARACTERIZATION OF SPLVS AND MLVS | | | |
|---|---|---|---|
| | Tau | S | A° |
| SPLVs | $2.65 \times 10^{-9}$ Sec | 0.614 | 14.9 |
| MLVs | $3.65 \times 10^{-9}$ Sec | 0.595 | 14.9 |

Thus the rate of nitroxide reduction can be used to study the rate of penetration of the ascorbate into lipid bilayers. FIG. 3 shows the percentage remaining spin versus time for SPLVs and MLVs suspended in an ascorbate solution. At 90 minutes the ascorbate has reduced 25% of the probe embedded in MLVs but 60% of the probe embedded in SPLVs. SPLVs allow for a dramatically greater penetrability of ascorbate than do MLVs.

5.2.5. Entrapment of Active Material by SPLVs

As another prime example of the superiority of SPLVs over traditional MLVs, SPLVs entrap a larger percentage of the available active material thereby conserving material (see Table V).

5.2.6. Interaction of SPLVs with Cells

Still another benefit of SPLVs is that SPLVs interact with cells such that a relatively large portion of the materials encapsulated inside the vesicle is dispersed throughout the cytoplasm of the cells rather than being limited to phagocytic vesicles.

TABLE V

| COMPARISON OF MLVS AND SPLVS | | |
|---|---|---|
| | % Available Material Entrapped | |
| Encapsulation of: | MLVs | SPLVs |
| inulin (aqueous space marker) | 2-6% | 20-30% |
| bovine serum albumin | 15% | 20-50% |
| streptomycin | 12-15% | 20-40% |
| polyvinylpyrrolidone (aqueous space) | 5% | 25-35% |

When SPLVs are mixed with cells the two appear to coalesce. By coalescence, SPLVs, unlike MLVs, interact with cells in vitro so that all the cells contain at least some of the materials originally entrapped in the SPLVs. This material appears to be distributed throughout each cell and not limited to just the phagocytic vesicles. This can be demonstrated by incorporating ferritin in the aqueous phase of a SPLV preparation. After coalescence with a cell in culture, ultrastructural analysis reveals that the ferritin is distributed throughout the cytosol and is not bound by intracellular membranes. While this phenomenon can be shown to occur with MLVs a greater quantity of material can be transferred by SPLVs.

5.2.7. Buoyant Density of SPLVs

Additionally, SPLVs have a lower buoyant density than MLVs. This is measured by banding in a ficol gradient (see Table VI).

5.2.8. Volume of SPLVs

Furthermore, when collected in a pellet by centrifugation from 1,000 to 100,000×g, SPLVs form a pellet that is substantially larger than MLVs, given the same phospholipid concentration. At a force of 16,000×g, the SPLVs form a pellet approximately one third larger than MLVs.

5.2.9. Osmotic Properties of SPLVs

Since ospholipid bilayers are permeable to water, placing MLVs in a hypertonic environment drives the occluded water out due to osmotic force. SPLVs shrink more than MLVs. In addition, after shrinking 16 hours in a buffer that is twenty times higher than the internal salt concentration, SPLVs do not shrink to the same final volume as MLVs (SPLV pellets remain ⅓ larger than MLV pellets). This indicates that the difference in pellet size is not due to differences in aqueous enclosed volume.

5.3. Uses of SPLVs

SPLVs are particularly useful in systems where the following factors are important: stability during storage and contact with body fluids; a relatively high degree of encapsulation; cost-effectiveness; and the release of the entrapped compound in its biologically active form.

TABLE VI

| BUOYANT DENSITY | | |
|---|---|---|
| | MLVs | SPLVs |
| in ficol | layers above 1% | layers above 0.5% |
| in gms/ml | 1.071 | 1.0274 |

Furthermore, depending upon the mode of administration in vivo, SPLVs can be resistant to rapid clearance (e.g., where sustained delivery is important) or can be delivered to the cells of the RES.

As a result, the SPLVs of the invention are usefully employed in a wide variety of systems. They may be used to enhance the therapeutic efficacy of medications, to cure infections, to enhance enzyme replacement, oral drug delivery, topical drug delivery, for introducing genetic information into cells in vitro and in vivo, for the production of vaccines, for the introduction of recombinant deoxyribonucleic acid segments into cells, or as diagnostic reagents for clinical tests following release of entrapped "reporter" molecules. The SPLVs can also be employed to encapsulate cosmetic preparations, pesticides, compounds for sustained slow release to effect the growth of plants and the like.

The methods which follow, while described in terms of the use of SPLVs, contemplate the use of SPLVs or any other liposome or lipid vesicle having functional characteristics similar to those of SPLVs.

5.3.1. Delivery of Bioactive Compounds

Delivery of compounds to cells in vitro (e.g., animal cells, plant cells, protists, etc.) generally requires the addition of the SPLVs containing the compound to the cells in culture. SPLVs, however, can also be used to deliver compounds in vivo in animals (including man), plants and protists. Depending upon the purpose of delivery, the SPLVs may be administered by a number of routes: in man and animals this includes but is not limited to injection (e.g., intravenous, intraperitoneal, intramuscular, subcutaneous, intraauricular, intramammary, intraurethrally, etc.), topical application (e.g., on afflicted areas), and by absorption through epithelial or mucocutaneous linings (e.g., ocular epithelia, oral mucosa, rectal and vaginal epithelial linings, the respiratory tract linings, nasopharyngeal mucosa, intestinal mucosa, etc.); in plants and protists this includes but is not limited to direct application to organism, dispersion in the organism's habitat, addition to the surrounding environment or surrounding water, etc.

The mode of application may also determine the sites and cells in the organism to which the compound will be delivered. For instance, delivery to a specific site of infection may be most easily accomplished by topical application (if the infection is external). Delivery to the circulatory system (and hence reticuloendothelial cells), may be most easily accomplished by intravenous, intraperitoneal, intramuscular, or subcutaneous injections.

Since SPLVs allow for a sustained release of the compound, doses which may otherwise be toxic to the organism may be utilized in one or more administrations to the organism.

The sections which follow describe some overall schemes in which SPLVs may be used and demonstrate but do not limit the scope of the present invention.

5.3.2. Treatment of Pathologies

A number of pathological conditions which occur in man, animals and plants may be treated more effectively by encapsulating the appropriate compound or compounds in SPLVs. These pathologic conditions include but are not limited to infections (intracellular and extracellular), cysts, tumors and tumor cells, allergies, etc.

Many strategies are possible for using SPLVs in the treatment of such pathologies; a few overall schemes are outlined below which are particularly useful in that they take advantage of the fact that SPLVs when administrered in vivo are internalized by macrophages.

In one scheme, SPLVs are used to deliver therapeutic agents to sites of intracellular infections. Certain diseases involve an infection of cells of the reticuloendothelial system, e.g., brucellosis. These intracellular infections are difficult to cure for a number of reasons: (1) because the infectious organisms reside within the cells of the reticuloendothelial system, they are sequestered from circulating therapeutic agents which cannot cross the cell membrane in therapeutically sufficient concentrations, and, therefore, are highly resistant to treatment; (2) often the administration of toxic levels of therapeutic agents are required in order to combat such infections; and (3) the treatment has to be completely effective because any residual infection after treatment can reinfect the host organism or can be transmitted to other hosts.

According to one mode of the present invention, SPLVs containing an appropriate biologically active compound are administered (preferably intraperitoneally or intravenously) to the host organism or potential host organism (e.g., in animal herds, the uninfected animals as well as infected animals may be treated). Since phagocytic cells internalize SPLVs, the administration of an SPLV-encapsulated substance that is biologically active against the infecting organism will result in directing the bioactive substance to the site of infection. Thus, the method of the present invention may be used to eliminate infection caused by a variety of microorganisms, bacteria, parasites, fungi, mycoplasmas, and viruses, including but not limited to: Brucella spp., Mycobacterium spp., Salmonella spp., Listeria spp., Francisella spp., Histoplasma spp., Corynebacterium spp., Coccidiodes spp. and lymphocytic choriomeningitis virus.

The therapeutic agent selected will depend upon the organism causing the infection. For instance, bacterial infections may be eliminated by encapsulating an antibiotic. The antibiotic can be contained within the aqueous fluid of the SPLV and/or inserted into the vesicle bilayer. Suitable antibiotics include but are not limited to: penicillin, ampicillin, hetacillin, carbencillin, tetracycline, tetracycline hydrochloride, oxytetracycline hydrochloride, chlortetracycline hydrochloride, 7-chloro-6-dimethyltetracycline, doxycycline monohydrate, methacycline hydrochloride, minocycline hydrochloride, rolitetracycline, dihydrostreptomycin, streptomycin, gentamicin, kanamycin, neomycin, erythromycin, carbomycin, oleandomycin, troleandomycin, Polymyxin B collistin, cephalothin sodium, cephaloridine, cephaloglycin dihydrate, and cephalexin monohydrate.

We have demonstrated the effectiveness of such treatments in curing brucellosis (see Examples, infra). By the procedure of this invention, the effectiveness and duration of action are prolonged. It is surprising that this system is effective for treating infections which do not respond to known treatments such as antibiotics entrapped in MLVs. Successful treatment is unexpected since any small remaining infections will spread and the infectious cycle will commence again. We have also demonstrated success in treating lymphocytic choriomeningitis virus infection.

Of course, the invention is not limited to treatment of intracellular infections. The SPLVs can be directed to a variety of sites of infection whether intracellular or extracellular. For instance, in another embodiment of the present invention, macrophages are used to carry an active agent to the site of a systemic extracellular infection. According to this scheme, SPLVs are used to deliver a therapeutic substance to uninfected macrophages by administering the SPLVs in vivo (preferably intraperitoneally or intravenously). The macrophages will coalesce with the SPLVs and then become "loaded" with the therapeutic substance; in general, the macrophages will retain the substance for approximtely 3 to 5 days. Once the "loaded" macrophages reach the site of infection, the pathogen will be internalized by the macrophages. As a result, the pathogen will contact the therapeutic substance contained within the macrophage, and be destroyed. This embodiment of the invention is particularly useful in the treatment of *Staphylococcus aureus* mastitis in man and cattle.

If the site of infection or affliction is external or accessible the SPLV-entrapped therapeutic agent can be applied topically. A particularly useful application involves the treatment of eye afflictions. In the case of ocular afflictions, SPLVs containing one or more appropriate active ingredients may be applied topically to the afflicted eye. A number of organisms cause eye infections in animals and man. Such organisms include but are not limited to: Moraxella spp., Clostridium spp., Corynebacterium spp., Diplococcus spp., Flavobacterium spp., Hemophilus spp., Klebsiella spp., Leptospira spp., Mycobacterium spp., Neisseria spp., Propionibacterium spp., Proteus spp., Pesudomonas spp., Serratia spp., Escherichia spp., Staphylococcus spp., Streptococcus spp. and bacteria-like organisms including Mycoplasma spp. and Rickettsia spp. These infections are difficult to eliminate using conventional methods because any residual infection remaining after treatment can reinfect through lacrimal secretions. We have demonstrated the use of SPLVs in curing ocular infections caused by *Moraxella bovis* (see examples, infra).

Because SPLVs are resistant to clearance and are capable of sustained release of their contents, SPLVs are also useful in the treatment of any affliction requiring prolonged contact with the active treating substance. For example, glaucoma is a disorder characterized by a gradual rise in intraocular pressure causing progressive loss of peripheral vision, and, when uncontrolled, loss of central vision and ultimate blindness. Drugs used in the treatment of glaucoma may be applied topically as eyedrops. However, in some cases treatment requires administering drops every 15 minutes due to the rapid clearing of the drug from the eye socket. If an affliction such as glaucoma is to be treated by this invention therapeutic substances as pilocarpine, Floropryl, physostigmine, carcholin, acetazolamide, ethozolamide, dichlorphenamide, carbachol, demecarium bromide, diisopropylphosphofluoridate, ecothioplate iodide, physostigmine, or neostigmine, etc. can be entrapped within SPLVs which are then applied to the affected eye.

Other agents which may be encapsulated in SPLVs and applied topically include but are not limited to: mydriatics (e.g., epinephrine, phenylepinephrine, hydroxy amphetamine, ephedrine, atropine, homatropine, scopolamine, cyclopentolate, tropicamide, encatropine, etc.); local anesthetics; antiviral agents (e.g., idoxuridine, adenine arabinoside, etc.); antimycotic agents (e.g., amphoteracin B, natamycin, pimaricin, flucytosine, nystantin, thimerosal, sulfamerazine, thiobendazole, tolnaftate, grisiofulvin, etc.); antiparasitic agents (e.g., sulfonamides, pyrimethamine, clindamycin, etc.); and anti-inflammatory agents (e.g., corticosteriods such as ACTH, hydrocortisone, prednisone, medrysone, beta methasone, dexamethasone, fluoromethalone, triamcinalone, etc.).

The following Examples are given for purposes of illustration and not by way of limitation on the scope of the invention.

6. EXAMPLE: PREPARATION OF SPLVS

As explained in Section 5.1. the basic method for preparing SPLVs involves dissolving a lipid or mixture of lipids into an organic solvent, adding an aqueous phase and the material to be encapsulated, and sonicating the mixture. In the preferred embodiment the solvent is removed during sonication; however, the organic solvent may be removed during or after sonication by any evaporative technique. The SPLVs used in all of the examples contained herein were prepared as described in the following subsections (however any method which yields SPLVs may be used).

6.1. SPLVs Containing Antibiotics

A 5 ml diethyl ether solution of 100 mg lecithin was prepared. The mixture was placed in a round-bottom flask. Then a solution (0.3 ml) containing 100 mg of streptomycin sulfate at pH 7.4 in 5 mM HEPES (4-[2-Hydroxyethyl]piperazino 2-ethane sulfonic acid)/0.0725 M NaCl/0.0725 M KCl was pipetted into the glass vessel containing the diethyl ether solution of lipid. The mixture was placed in a bath sonicator (Laboratory Supplies Co., Inc.) type 10536 for several minutes, (80 kH$_z$ frequency:output 80 watts) while being dried to a viscous paste by passing thereover a gentle stream of nitrogen.

To the viscous paste remaining was added 10 ml of 5 mM HEPES. The resulting SPLV preparation, containing streptomycin, was suspended in the buffer solution, shaken for several minutes on a vortex mixer, and freed of non-encapsulated streptomycin by centrifuging at 12,000 ×g for 10 minutes at 20° C. The resulting cake was suspended in 0.5 ml of 5 mM HEPES.

The procedure described above was followed except that streptomycin was substituted by each one of the following: dihydrostreptomycin, gentamycin sulfate, ampicillin, tetracyline hydrochloride, and kanamycin.

6.2. SPLVs Containing Other Membrane Constituents

The process described in Section 6.1. was followed except that any one of the following was added with the egg lecithin: (1) phosphatidic acid to give a molar ratio of 8:2 (lecithin:dicetylphosphate); (2) stearylamine to give a molar ratio of 8:2 (lecithin: stearylamine); cholesterol and stearylamine to give a molar ratio of 7:2:1 (lecithin:cholesterol:stearylamine); and (3) phosphatidic acid and cholesterol to give a molar ratio of 7:2:1 (lecithin:phosphatidic acid:cholesterol).

6.3. SPLVs Containing Pilocarpine

The procedure of Section 6.1. was followed except that the antibiotic streptomycin was replaced with pilocarpine.

6.4. SPLVs Prepared With and Without BHT

Undistilled ether contains an anti-oxidant, 1 μg/ml butylhydroxytoluene (BHT), for storage purposes. The procedure described in Section 6.1. was following using undistilled ether as the solvent in order to incorporate BHT into the SPLV preparation.

In order to prepare SPLVs without incorporation of BHT, the procedure described in Section 6.1. was followed using distilled ether as the solvent.

7. EXAMPLE: SPLV MEDIATED DELIVERY IN VITRO

In the following example, SPLV mediated delivery of antibiotics to macrophages in culture was demonstrated.

Peritoneal macrophages were obtained by peritoneal lavage from $C_{57}BLK$ adult male mice and suspended in minimal essential medium (M.E.M.) pH 7.2 containing 10% heat-inactivated fetal calf serum. Cells were suspended at a concentration of $1 \times 10^6$ cells per ml in 96-well tissue culture dishes. To cultures containing adherent peritoneal macrophages, were added *B. canis* at concentrations of $1 \times 10^6$ CFU (colony forming units) per ml. After 12 hours, bacteria not engulfed by peritoneal macrophages were removed by repeated washings with M.E.M. After washing of peritoneal macrophage cultures, they were divided into 5 groups, each containing 12 replicate cultures per group. Group 1, designated Controls, received no treatment. Group 2 received aqueous streptomycin sulfate at a concentration of 1 mg/ml. Group 3 received buffer-filled SPLVs. Group 4 received aqueous streptomycin sulfate (1 mg/ml) plus preformed buffer-filled SPLVs. Group 5 received SPLVs containing streptomycin sulfate (1 mg/ml). After 24 hours, supernatants were removed by repeated washings and peritoneal macrophages were disrupted by repeated freezing and thawing. Serial dilutions of disrupted macrophages were plated onto brucella agar and, after 4 days, surviving *B. canis* were determined by limiting dilution techniques. Results shown in Table VII indicate that SPLV-entrapped streptomycin was totally effective in killing and eliminating the intracellular *B. canis* infection in vitro.

The experiment was repeated with *B. abortus* exactly as described above except that peritoneal macrophages were obtained by peritoneal lavage from adult female albino guinea pigs. Results are also shown in Table VII.

TABLE VII

COLONY-FORMING UNITS OF INTRACELLULAR BRUCELLA ISOLATED AFTER TREATMENT OF INFECTED MACROPHAGES WITH SPLVS CONTAINING STREPTOMYCIN

| | *B. canis*[a] | *B. abortus*[b] |
|---|---|---|
| Controls | $2.6 \pm 1.13 \times 10^3$ | $3.1 \pm 0.81 \times 10^4$ |
| Buffer-filled SPLVs | $2.82 \pm 0.10 \times 10^3$ | $2.9 \pm 0.17 \times 10^4$ |
| Free Streptomycin[c] | $3.11 + 0.40 \times 10^3$ | $3.3 \pm 0.25 \times 10^4$ |
| Streptomycin Plus Buffer-filled SPLVs[c] | $2.76 \pm 0.20 \times 10^3$ | $2.8 \pm 0.42 \times 10^4$ |
| SPLV-Entrapped Streptomycin[c] | 0 | 0 |

[a]Colony forming units (CFU) of *B. canis* (mean ± SD of 12 replicates) isolated from equal numbers of previously infected mouse ($C_{57}$Blk) peritoneal macrophages.
[b]CFU of *B. abortus* (mean ± SD of 12 replicates) isolated from equal numbers of previously infected guinea pig peritoneal macrophages.
[c]Concentration of streptomycin 1 mg/ml.

8. EXAMPLE: TREATMENT INTRACELLULAR INFECTIONS

The following examples demonstrate how SPLVs can be used in treating intracellular infections. The data presented demonstrates: (1) the effectiveness of using antibiotics encapsulated in SPLVs in the treatment of disease and (2) the greater efficiency which is obtained by administering multiple doses of the SPLV preparation. A comparison of MLVs to SPLVs as vehicles used in the protocols is described.

Brucellosis causes worldwide economic and public health problems. Brucellosis is caused by Brucella spp. It is adapted to many mammalian species, including man, domestic animals and a variety of wild animals. Six Brucella spp. cause brucellosis in animals; they are *B. abortus, B. canis, B. melitensis, B. neotomae, B. ovis* and *B. suis.* Both domestic and wild animals serve as reservoirs for potential spread of brucellosis to other animals and man.

Such infections cannot be cleared with antibiotics because the infectious organisms reside within the cells of the reticuloendothelial system and are highly resistant to bactericidal activities of antibiotics. The quantity of antibiotics required and the length of treatment results in either toxic effects on the animal or an unacceptably high concentration of the antibiotic in the tissues of the animal. The further difficulty in treating this disease is that the treatment has to be completely effective since any remaining infection will simply spread and the cycle commences once again. The economic impact of such diseases is demonstrated by the millions of dollars of valuable cattle which are lost each year due to spontaneous abortion. The only potential way to combat such infectious outbreaks is to quarantine and then slaughter the animals.

The examples which follow comprise incorporating an antibiotic into SPLVs, and then administrating the encapsulated active substance to the animals by inoculating the infected animals intraperitoneally.

8.1. Effect of a Single Treatment of *B. Canis* Infection Using SPLV-Entrapped Antibiotic Eighty adult male Swiss mice were infected intraperitoneally (I.P.) with *B. canis* ATCC 23365 ($1\times10^7$ CFU) and divided into 8 groups of 10 mice each. Seven days post-inoculation with *B. canis,* groups were treated as follows: Group 1, designated Controls, received no treatment; Group 2 received buffer-filled SPLVs (0.2 ml I.P.); Group 3 received aqueous streptomycin sulfate (1 mg/kg body weight in a total administration of 0.2 ml I.P.); Group 4 received aqueous streptomycin sulfate (5 mg/kg body weight) in a total administration of 0.2 ml I.P.; Group 5 received aqueous streptomycin sulfate (10 mg/kg body weight) in a total administration of 0.2 ml I.P.; Group 6 received SPLVs containing streptomycin sulfate (1 mg/kg body weight) in a total administration of 0.2 ml I.P.; Group 7 received SPLVs containing streptomycin sulfate (5 mg/kg body weight) in a total administration of 0.2 ml I.P.; and Group 8 received SPLVs containing streptomycin sulfate (10 mg/kg body weight) in a total administration of 0.2 ml I.P.. On day 14 post-inoculation with *B. canis,* all animals were sacrificed and spleens were removed aseptically. Spleens were homogenized and serially diluted onto brucella agar to determine the number of surviving *B. canis* in spleens after treatment. Results after 4 days incubation are shown in Table VIII.

TABLE VIII

EFFECT OF A SINGLE TREATMENT[a] OF *B. CANIS* INFECTED MICE WITH VARIOUS CONCENTRATIONS OF FREE OR SPLV-ENTRAPPED STREPTOMYCIN

Colony-Forming Units *B. Canis* Per Spleen

TABLE VIII-continued EFFECT OF A SINGLE TREATMENT[a] OF *B. CANIS* INFECTED MICE WITH VARIOUS CONCENTRATIONS OF FREE OR SPLV-ENTRAPPED STREPTOMYCIN

|  | No Treatment | Buffer-Filled SPLVs[b] |
|---|---|---|
| Control | $3.46 \times 10^6 \pm 2.7 \times 10^6$ | $4.1 \times 10^6 \pm 0.66 \times 10^6$ |
| Streptomycin Concentration (mg/kg body weight) | Free Streptomycin | SPLV-Entrapped Streptomycin |
| 1 | $1.5 \pm 0.45 \times 10^6$ | $1.01 \pm 0.25 \times 10^3$ |
| 5 | $2.12 \pm 1.71 \times 10^5$ | $1.52 \pm 0.131 \times 10^4$ |
| 10 | $9.66 \pm 3.68 \times 10^4$ | $1.32 \pm 1.00 \times 10^4$ |

[a]I.P. injection in total of 0.2 ml (sterile saline).
[b]Surviving *B. canis* was determined as the number of CFU isolated per spleen and is expressed as mean ± S.D. of 10 animals per experiment (triplicate experiments).

8.2. Effect of Multiple Treatment of *B. Canis* Infection Using SPLV-Entrapped Antibiotic Eighty adult male Swiss mice were infected with *B. canis* ATCC 23365 ($1 \times 10^7$ CFU, I.P.) and divided into 8 groups of 10 mice each. Seven and 10 days post-inoculation with *B. canis*, groups were treated as follows: Group 1, designated controls, received no treatment; Group 2 received buffer-filled SPLVs (0.2 ml, I.P.); Group 3 received aqueous streptomycin sulfate (1 mg/kg body weight) in a total administration of 0.2 ml, I.P.); Group 4 received aqueous streptomycin sulfate (5 mg/kg body weight) in a total administration of 0.2 ml, I.P.; Group 5 received aqueous streptomycin sulfate (10 mg/kg body weight) in a total administration of 0.2 ml, I.P.; Group 6 received SPLVs containing streptomycin sulfate (1 mg/kg body weight) in a total administration of 0.2 ml, I.P.; Group 7 received SPLVs containing streptomycin sulfate (5 mg/kg body weight) in a total administration of 0.2 ml, I.P.; and Group 8 received SPLVs containing streptomycin sulfate (10 mg/kg body weight) in a total administration of 0.2 ml, I.P. On day 14 post-inoculation with *B. canis*, all animals were sacrificed and spleens were removed aseptically. Spleens were homogenized and serially diluted onto brucella agar to determine the number of surviving *B. canis* in spleens after treatment. Results after 4 days incubation are shown in FIG. 5.

The results of various two-stage treatment regimens on *B. canis* infections in vivo presented in FIG. 5, demonstrate that in groups receiving aqueous streptomycin 7 and 10 days post-inoculation, very little reduction in surviving *B. canis* in spleens was observed. Only in groups receiving SPLV-entrapped streptomycin at a concentration of 10 mg/kg body weight administered on day 7 and 10 post-inoculation were all viable bacterial eliminated from spleens of infected animals.

In addition to the experiment described above, various tissues from *B. canis* infected mice after two treatments with SPLV-entrapped streptomycin were sampled as follows:

Thirty adult male Swiss mice were inoculated with *B. canis* ATCC 23365 ($1\times10^7$ CFU, I.P.). Seven days post-inoculation animals were divided into 3 groups of 10 mice each. Group 1, designated controls, received no treatment; Group 2 received (on days 7 and 10 post-inoculation) aqueous streptomycin sulfate (10 mg/kg body weight) in each administration of 0.2 ml), I.P.; Group 3 received (on days 7 and 10 post-inoculation) SPLVs containing streptomycin sulfate (10 mg/kg body weight) in each administration of 0.2 ml, I.P. On days 14 to 75 post-inoculation with *B. canis*, all animals were sacrificed and the following organs removed aseptically, homogenized and serially diluted onto brucella agar for isolation of *B. canis:* heart, lungs, spleen, liver, kidneys, testes. After 4 days incubation, results of surviving *B. canis* per organ are shown in FIG. 6.

Results of samplings of various tissues in *B. canis* infected mice after two treatment regimens with streptomycin presented in FIG. 6, demonstrated that in animals treated with SPLV-entrapped streptomycin, all tissues sampled from 14 to 75 days post-inoculation with *B. canis* were totally free of any viable *B. canis* organisms. In animals untreated or treated with aqueous streptomycin in concentrations and administration schedules identical to those receiving SPLV-entrapped streptomycin, viable *B. canis* organisms could be isolated in all tissues sampled from 14 to 75 days post-inoculation with *B. canis.* b 8.3. Effectiveness of Treatments Using MLVs as Compared to SPLVs

Fifteen adult male Swiss mice were inoculated with *B. canis* ATCC 23365 ($1\times10^7$ CFU, I.P.). Seven days post-inoculation animals were divided into 3 groups of 5 mice each. Group 1, designated Controls, received no treatment; Group 2 received (on days 7 and 10 post-inoculation) MLVs containing streptomycin sulfate (10 mg/kg body weight, I.P.). MLVs were prepared by conventional techniques using 100 mg egg phosphatidylcholine (EPC) and 2 ml of sterile HEPES containing streptomycin sulfate (100 mg/ml). The lipid to streptomycin sulfate ratio was 100 mg EPC to 28 mg streptomycin sulfate in the 2 ml final MLV suspension; Group 3 received (on days 7 and 10 post-inoculation) SPLVs containing streptomycin sulfate (10 mg/kg body weight, I.P.) prepared as described in Section 6.1. with the following modifications: 100 mg EPC were used, and 0.3 ml of HEPES containing 100 mg streptomycin sulfate. The lipid to streptomycin sulfate ratio in SPLVs was 100 mg EPC to 28 mg streptomycin sulfate in a 2 ml final suspension. On day 14 post-inoculation with *B. canis*, all animals were sacrificed and spleens were removed aseptically, homogenized and serially diluted onto brucella agar for isolation of *B. canis.* Results of surviving *B. canis* per organ after 4 days incubation are shown in Table IX.

8.4. Effect of Various SPLV-Entrapped Antibiotics on Treatment of Infection

Fifty adult male Swiss mice were inoculated with *B. canis* ATCC 23365 ($1\times10^7$ CFU, I.P.). Seven days post-inoculation, animals were divided into 10 groups of 5 mice each. Group 1, designated controls, received no treatment; Group 2 received buffer-filled SPLVs (0.2 ml, I.P.) on days 7 and 10 post-inoculation; Groups 3, 4, 5 and 6 received aqueous injections (0.2 ml I.P.) of dihydrostreptomycin, gentamycin, kanamycin or streptomycin 10 mg/kg body weight, I.P. on days 7 and 10 post-inoculation (N.B. Each of these antibiotics have been shown to kill *B. canis* in vitro).

TABLE IX

| COMPARISON OF MLVS AND SPLVS CONTAINING STREPTOMYCIN SULFATE ON KILLING OF *B. CANIS* IN VIVO AFTER TWO TREATMENTS[a] | |
|---|---|
| | Colony-Forming Units *B. Canis* per Spleen[b] |
| Control | $2.7 \pm 1.0 \times 10^4$ |

TABLE IX-continued
COMPARISON OF MLVS AND SPLVS CONTAINING STREPTOMYCIN SULFATE ON KILLING OF B. CANIS IN VIVO AFTER TWO TREATMENTS[a]

| | Colony-Forming Units B. Canis per Spleen[b] |
|---|---|
| MLVs[c] | $1.8 \pm 0.4 \times 10^4$ |
| SPLVs[c] | 0 |

[a]Intraperitoneal injections, 10 mg/kg body weight, were spaced at 3 day intervals. Controls received no treatment.
[b]Surviving B. canis was determined as the number of CFU isolated per spleen and is expressed as the mean ± S.D. of 5 animals per group (duplicate determinations per animal).
[c]Egg phosphatidylcholine to streptomycin sulfate ratios were 100 mg lipid to 28 mg streptomycin sulfate.

Groups 7, 8, 9, and 10 received SPLVs containing dihydrostreptomycin, gentamicin, kanamycin, or streptomycin at 10 mg/kg body weight on days 7 and 10 post-inoculation. On day 14 post-inoculation with *B. canis*, all animals were sacrificed and spleens were removed aseptically, homogenized and serially diluted onto brucella agar for at isolation of *B. canis*. Results of surviving *B. canis* per organ after 4 days incubation are as shown in Table X.

TABLE X

COMPARISON OF VARIOUS ANTIBIOTICS ON KILLING OF *B. CANIS* IN VIVO AFTER TWO TREATMENTS[a]

| | Colony-Forming Units *B. Canis* Per Spleen[b] | |
|---|---|---|
| | Aqueous Solutions | SPLV-Entrapped Antibiotic |
| Untreated | $3.93 \pm 1.51 \times 10^6$ | $4.66 \pm 0.87 \times 10^6$ |
| Antibiotic[c] | | |
| Dihydrostreptomycin | $1.13 \pm 0.30 \times 10^5$ | 0 |
| Gentamycin | $7.06 \pm 2.53 \times 10^5$ | 0 |
| Kanamycin | $2.72 \pm 0.91 \times 10^5$ | 0 |
| Streptomycin | $1.01 \pm 0.17 \times 10^5$ | 0 |

[a]Intraperitoneal treatments, 10 mg/kg body weight, were spaced at 3 day intervals. Controls received no treatment.
[b]Surviving *B. canis* per organ was determined as the number of CFU isolated per spleen and expressed as the mean ± S.D. of 5 animals per groups (duplicate determinations per animal).
[c]Antibiotics effective in killing *B. canis* in suspension culture.

The results from tests of various antibiotics on *B. canis* infected mice presented in Table X demonstrate that antibiotics which are effective in killing *B. canis* in vitro (i.e., in suspension culture) are also only effective in killing *B. canis* infections in vivo when they are encapsulated within SPLVs. Animals receiving either aqueous antibiotics, buffer-filled SPLVs or no treatment were in no case cleared of surviving *B. canis* in isolated spleen tissues.

8.5 Treatment of Dogs Infected with *B. canis*

Adult female beagles were inoculated with *B. canis* ATCC 23365 ($1 \times 10^7$ CFU) orally and vaginally. Seven days post-inoculation dogs were divided into 3 groups. Group 1, designated control, received no treatment; Group 2 received (on days 7 and 10 post-inoculation) aqueous streptomycin sulfate at 10 mg/kg body weight (each administration was 5.0 ml, I.P.). Group 3 received (on days 7 and 10 post-inoculation) SPLVs containing streptomycin sulfate at 10 mg/kg body weight (each administration was 3.0 ml, I.P.). Vaginal swabbings of dogs and heparinized blood samples were collected at regular intervals before, during, and at the termination of the study. These were cultured on brucella agar in order to isolate *B. canis*. Results are shown in Table XI. Serum samples were collected before, during, and at the termination of the study for determinations of serum antibody against *B. canis*. These results are also shown in Table XI. Twenty-one days post-inoculation with *B. canis*, all animals were euthanized. The following tissues were removed aseptically, homogenized and serially diluted onto brucella agar for isolation of *B. canis*: heparinized blood, vaginal exudate, lungs, spleen, synovial fluid, uterus, ovary, popliteal lymph nodes, salivary glands, tonsils, mediastinal lymph nodes, mesenteric lymph nodes, bone marrow, superficial cervical lymph nodes, and auxiliary lymph nodes. Results of surving *B. canis* per tissue after 4 days incubation are shown in Table XII.

TABLE XI

RESULTS OF CULTURES AND SEROLOGICAL TESTING IN *B. CANIS* INFECTED DOGS SUBJECTED TO A TWO TREATMENT ANTIBIOTIC REGIMEN[a]

| Days After Infection with *B. Canis* | Control | | | | Streptomycin[b] | | | | SPLV-Entrapped Streptomycin[c] | | | |
|---|---|---|---|---|---|---|---|---|---|---|---|---|
| | R | M | B | V | R | M | B | V | R | M | B | V |
| Pre-treatment | | | | | | | | | | | | |
| 0 | 0 | 0 | 0 | 0 | 0 | 0 | 0 | 0 | 0 | 0 | 0 | 0 |
| 2 | ND | ND | + | + | ND | ND | + | 0 | ND | ND | + | + |
| 4 | ND | ND | + | + | ND | ND | + | + | ND | ND | + | + |
| Post-treatment | | | | | | | | | | | | |
| 8 | 0 | 0 | 0 | + | 0 | 0 | + | 0 | 0 | 0 | 0 | 0 |
| 10 | 0 | 0 | 0 | + | 0 | 0 | 0 | + | 0 | 0 | 0 | 0 |
| 21 | 1.5 | 2 | + | + | 1 | 2 | + | + | 0 | 0 | 0 | 0 |

[a]R (rapid slide agglutination test) indicates the reciprocal of serum titer to *B. canis* antigen ($\times 10^2$); 0 = no detectable titer.
M (2-mercaptoethanol tube agglutination test) indicates the reciprocal of serum titer to *B. canis* antigen ($\times 10^2$); 0 = no detectable titer.
In B (blood culture) and V (vaginal culture) on brucella agar: + = detection of greater than or equal to 1 CFU; 0 = no colonies detected. Controls received no treatment.
[b]Streptomycin sulfate (aqueous) 10 mg/kg body weight, I.P.
[c]SPLVs containing streptomycin sulfate 10 mg/kg body weight, I.P.

TABLE XII

RESULTS OF CULTURES FROM TISSUE SAMPLES IN *B. CANIS* INFECTED DOGS SUBJECTED TO A TWO TREATMENT ANTIBIOTIC REGIMEN[a]

| Tissue[b] | SPLVs Containing Streptomycin[c] | Streptomycin[d] | Control[e] |
|---|---|---|---|
| Whole blood | 0 | + | + |
| Vaginal swab | 0 | + | + |
| Lungs | 0 | + | + |
| Spleen | 0 | + | + |
| Synovial fluid | N.D. | 0 | 0 |
| Uterus | 0 | + | + |

TABLE XII-continued
RESULTS OF CULTURES FROM TISSUE SAMPLES IN *B. CANIS* INFECTED DOGS SUBJECTED TO A TWO TREATMENT ANTIBIOTIC REGIMEN[a]

| Tissue[b] | SPLVs Containing Streptomycin[c] | Streptomycin[d] | Control[e] |
|---|---|---|---|
| Ovary | 0 | + | + |
| Popliteal lymph node | N.D. | + | + |
| Salivary gland | 0 | 0 | 0 |
| Tonsil | 0 | + | + |
| Mediastinal lymph node | 0 | N.D. | + |
| Mesenteric lymph node | N.D. | 0 | 0 |
| Bone marrow | 0 | + | + |
| Superficial cervical lymph node | N.D. | N.D. | + |
| Axillary lymph node | 0 | + | + |

[a]Animals treated on day 7 and 10 post-infection.
[b]Samples taken at necropsy were serially diluted on brucella agar; + = equal to or greater than 1 CFU; 0 = no colonies.
[c]SPLVs containing streptomycin sulfate, 10 mg/kg body weight, I.P.
[d]Streptomycin sulfate (aqueous), 10 mg/kg body weight, I.P.
[e]Controls received no treatment.

Results of culture and serologic tests of dogs infected with *B. canis* before, during, and after two-stage antibiotic administration are presented in Table XI. All animals were serologically negative for previous exposure to *B. canis* as measured by negative serum titers, and were culture negative from blood cultures and cultures of vaginal swabbings. All animals were noted to be culture positive for both blood and vaginal cultures prior to treatments on days 7 and 10. Dogs treated with aqueous streptomycin or dogs receiving no treatment remained culture positive for blood and vaginal cultures during post-treatment periods prior to termination on day 21. Group 3, which received liposomes containing streptomycin, became culture negative one day after the first treatment and remained negative throughout post-treatment period. Dogs which received no treatment or aqueous streptomycin developed detectable serum titers against *B. canis* antigens by day 21 post-inoculation, while those treated with SPLVs containing antibiotics on days 7 and 10 post-inoculation did not develop any detectable antibody to *B. canis* antigen.

Results from isolation of *B. canis* from infected dogs treated with two-stage antibiotic administration which are presented in Table XII demonstrate that in dogs, only treatment with SPLVs containing streptomycin was effective in eliminating any viable *B. canis* in all tissues from all organ samples.

8.6. Treatment of *B. Abortus* in Guinea Pigs

Fifteen adult female guinea pigs were inoculated with *B. abortus* ATCC 23451 ($1\times10^7$ CFU, I.P.). Seven days post-inoculation animals were divided into 3 groups of 5 animals each. Group 1, designated Controls, received no treatment. Group 2 received aqueous streptomycin sulfate, I.P. injections (0.2 ml) at 10 mg/kg body weight on day 7 and 10 post-inoculation with *B. abortus.* Group 3 received SPLVs containing streptomycin sulfate I.P. injections (0.2 ml) at 10 mg/kg body weight on days 7 and 10 post-inoculation with *B. abortus.* On day 14 post-inoculation with *B. abortus,* all animals were sacrificed and spleens were removed, aseptically homogenized and serially diluted onto brucella agar for isolation of *B. abortus.* Results of surviving *B. abortus* per spleen after 4 days incubation, are shown in FIG. 7. Only SPLVs containing streptomycin were effective in eliminating *B. abortus* residing within guinea pig spleen. In animals receiving aqueous streptomycin or no treatment, viable *B. abortus* bacteria were be identified.

8.7. Treatment of *B. abortus* Infection in Cows

Nine heavily infected animals were utilized in this experiment. *B. abortus* bacterial isolations from milk and vaginal swabbings became and remained negative for six weeks following treatment with SPLVs containing streptomycin. When infection reoccurred in these animals, bacterial isolations were found only in quadrants of the udder which were positive prior to treatment.

Nine cross-bred (hereford-jersey-Brangus), 22-month old, non-gravid, confirmed *B. abortus* culture-positive cows were used. At least 4 months prior to the initiation of the study, the animals were experimentally challenged per conjunctivum with $1\times10^7$ CFU of *B. abortus* Strain 2308 during mid-gestation, which resulted in abortion and/or *B. abortus* culture positive lacteal or uterine secretions and/or fetal tissues.

Cows were maintained in individual isolation stalls and separated into three groups. Treatment comprised a two-dose regimen, spaced 3 days apart, as follows: (1) 3 cows were injected intraperitoneally with physiological saline. (2) 3 cows were injected intraperitoneally with aqueous antibiotic (streptomycin at 10 mg/kg body weight) plus preformed buffer-filled SPLVs. (3) 3 cows were injected intraperitoneally with SPLV-entrapped streptomycin (10 mg/kg body weight). The total volume per injection was 100 ml per animal.

During the first 2 months duplicate bacteriologic cultures of lacteal and uterine secretions were performed weekly providing secretions were obtainable. Then, all 5 cows were euthanatized with an overdose of sodium pentabarbitol, and the following organs were collected in duplicate for bacteriologic cultures: (1) lymph nodes: left and right atlantal, left and right suprapharyngeal, left and right mandibular, left and right parotid, left and right prescapular, left and right prefemoral, left and right axillary, left and right popliteal, left and right internal iliac, left and right supramammary, left and right renal, bronchial, mediastinal, mesenteric, and hepatic; (2) glands: all four quarters of mammary gland, left and right adrenal glands and thymus (if present); (3) organs and other tissues: spleen, liver, left and right horn of uterus, cervix, vagina, kidney and tonsil.

After necropsy, all tissues were frozen and maintained at −70° C. while in transport. Tissues were thawed, alcohol flamed, and aseptically trimmed prior to weighing. Once weights were recorded (0.2 to 1.0 grams), the tissue was homogenized in 1 ml of sterile saline and serially diluted with sterile saline to $1:10^{-10}$ of initial homogenate suspension. Aliquots (20 μl) of each dilution from serial suspensions were plated onto brucella agar and placed in 37° C. incubation. Duplicate determinations were performed for each tissue.

Plates were read daily and scored for bacterial growth. All colonies appearing prior to 3 days were isolated, passaged, and gram stained to determine identity. On days 5, 6 and 7 during incubation colonies with morphology, growth, and gram staining characteristics consistent with *B. abortus* were counted; the CFU per gram tissue was then determined. Representative colonies were repassaged for bacterial confirmation of *B. abortus.*

Bacteriologic isolations were done on all tissue samples and quantitation of bacteria per gram of tissue were calculated. The results from four animals—one placebo control and three animals treated with SPLV-entrapped streptomycin—are presented in Table XIII.

EXAMPLE: TREATMENT OF OCULAR AFFLICTIONS

Bacterial and like infections as well as many other afflictions of the eye cause worldwide economic and public health problems, leading, if untreated or improperly treated, to loss of sight and possible death due to septicemia. Bacterial infections of the eye in animals and man have been reported to be caused by a variety of bacteria including but not limited to: Clostridium spp., Corynebacterium spp., Leptospira spp., Moraxella spp., Mycobacterium spp., Neisseria spp., Propionibacterium spp., Proteus spp., Pseudomonas spp., Serratia spps., E. Coli spp., Staphylococcus spp., Streptococcus spp. and bacteria-like organisms including Mycoplasma spp. and Rickettsia spp. Both animals and man serve as reservoirs for potential spread of infectious bacteria to each other.

TABLE XIII

RESULTS OF CULTURES FROM TISSUE SAMPLES OF *B. ABORTUS* INFECTED COWS

| Tissue | Untreated Control | SPLV-Entrapped Streptomycin 1 | 2 | 3 |
|---|---|---|---|---|
| Adrenal gland L | 0 | 0 | 0 | 0 |
| Adrenal gland R | ++ | 0 | 0 | + |
| Atlantal LN R | ++ | + | 0 | + |
| Atlantal LN L | 0 | 0 | 0 | + |
| Axillary LN R | +++ | 0 | + | 0 |
| Axillary LN L | ++ | 0 | 0 | 0 |
| Bronchial LN | 0 | 0 | 0 | 0 |
| Cervix | 0 | 0 | 0 | 0 |
| Hepatic LN | ++++ | 0 | 0 | 0 |
| Horn of Uterus L | 0 | 0 | 0 | + |
| Horn of Uterus R | 0 | 0 | 0 | 0 |
| Int. Illiac LN R | ++ | 0 | 0 | 0 |
| Int. Illiac LN L | ++++ | 0 | + | 0 |
| Kidney | 0 | 0 | 0 | 0 |
| Liver | 0 | 0 | 0 | 0 |
| Lung | 0 | 0 | 0 | 0 |
| Mammary Gland LF | 0 | + | + | 0 |
| Mammary Gland LR | 0 | 0 | 0 | + |
| Mammary Gland RF | ++ | 0 | 0 | 0 |
| Mammary Gland RR | ++ | 0 | 0 | 0 |
| Mandibular LN R | +++ | 0 | 0 | 0 |
| Mandibular LN L | +++ | 0 | 0 | 0 |
| Mediastinal LN | ++ | 0 | + | 0 |
| Mesenteric LN | +++ | 0 | 0 | 0 |
| Parotid LN L | +++ | 0 | 0 | 0 |
| Parotid LN R | +++ | 0 | 0 | 0 |
| Popliteal LN L | + | 0 | 0 | 0 |
| Popliteal LN R | + | 0 | 0 | 0 |
| Prefemoral LN L | + | 0 | 0 | 0 |
| Prefemoral LN R | 0 | 0 | 0 | 0 |
| Prescapular LN L | 0 | 0 | 0 | + |
| Prescapular LN R | ++++ | 0 | 0 | 0 |
| Renal LN | 0 | 0 | 0 | 0 |
| Spleen | +++ | 0 | 0 | 0 |
| Supramammary LN L | +++ | + | 0 | 0 |
| Supramammary LN R | 0 | 0 | 0 | 0 |
| Suprapharangeal LN L | + | 0 | 0 | 0 |
| Suprapharangeal LN R | 0 | 0 | 0 | 0 |
| Thymus | 0 | 0 | 0 | 0 |
| Vagina | +++ | 0 | 0 | 0 |

0 No detectable bacteria by culture of 0.3-1 gm of tissue.
+ Less than 200 colonies/gm tissue.
++ More than 300 colonies/gm.
+++ More than 1,000 colonies/gm.
++++ More than 100,000 colonies/gm.

Such bacterial infections cannot be treated with antibiotics without lengthy and cumbersome treatment schedules resulting in either frequent treatments, as rapid as every twenty minutes in humans with some infections, or unacceptably high concentrations of the antibiotic in the tissues. Current treatment methods are difficult for many other reasons. The infectious organism in the surface tissues of the eye in some cases are highly resistant to bactericidal activities of antibiotics, and topical administration of antibiotics can result in rapid clearing of the drug from the eye socket yielding varying contact times. As a general rule, treatment of eye infections has to be completely effective since any remaining infection will simply reinfect through lacrimal secretions and the cycle commences once again. Further, in many cases drug concentrations needed to eliminate the infection can cause impairment of vision and in certain cases can result in total blindness. The economic impact of such diseases in domestic animals is demonstrated by the millions of dollars which are lost each year since the only potential way to combat such infectious diseases is sustained therapy and quarantine.

The following experiments evaluate the effectiveness of treatments using free antibiotic in glycerine as compared to antibiotic entrapped in SPLVs for *M. bovis* infections of the eye.

*M. bovis* causes infectious keratoconjunctivitis (pinkeye) in cattle. This condition is characterized by blepharospasm, lacrimation, conjunctivitis and varying degrees of corneal opacity and ulceration. Adult cows may develop a mild fever with slightly decreased appetite and a decreased milk production. Although a number of antibiotics are effective against *M. bovis,* they must be administered early and repeated often by topical application or subconjuctival injection.

According to the examples described herein, the effectiveness and duration of action of the therapeutic substance are prolonged. It is surprising that this sytem is effective with only one or two administrations since such infections do not respond to simple ordinary treatment with antibiotics. The usual treatments often leave small remaining infections which reinfect the eye so that the infectious cycle will commence again, unless the infection is completely eradicated by numerous repetitions of the treatment.

9.1. Treatment of Infectious Keratoconjunctivitis in Mice

C57 black mice (160 mice) were divided into 8 groups. One half of each group was exposed to U.V. irradiation in each eye (in order to create corneal lesions). All animals were then inoculated with *M. bovis* instilled onto the right eye at concentrations of $1\times10^6$ bacteria per eye. Twenty-four hours post-inoculation all animals were scored for degree of corneal opacity. The eight groups were treated by topical application of the following to each eye: Groups 1 and 2 received 10 $\mu$l of SPLV-entrapped streptomycin (30 mg/ml); Groups 3 and 4 received 10 $\mu$l streptomycin (100 mg/ml); Groups 5 and 6 received 10 $\mu$l of buffer-filled SPLVs suspended in aqueous streptomycin (100 mg/ml); and Groups 7 and 8 received 10 $\mu$l of sterile saline (N.B. The uninfected left eyes were treated with the same topical solutions in order to determine whether SPLVs would irritate the eye; no irritation was observed). Once daily, animals were scored for progression or regression of corneal lesions and on days 3, 5 and 7 post-treatment right eyes were swabbed and isolations for *M. bovis* were performed on representative animals. *M. bovis* colonies were determined by colony morphology and reactivity to fluorescently labeled antibody to *M. bovis* pili. Results, shown in Table XIV, reveal that only the SPLV-entrapped streptomycin was effective in eliminating infection.

9.2 Treatment of Rabbit Conjunctiva Using SPLV-Entrapped Antibiotic

*M. bovis*, ATCC strain 10900, were diluted to a concentration of $1 \times 10^7$ cells per ml in sterile saline (0.085% NaCl). Aliquots (0.1 ml) of bacterial suspensions were inoculated topically into the eyes of ten adult female rabbits. Samples for cultures were taken daily by swabbing the conjunctivae and plated onto blood agar plates for isolation of *M. bovis*. Three days post-inoculation, rabbits were divided into 3 groups: 2 animals (controls) received no treatment; 4 animals received streptomycin in sterile saline (concentration 10 mg/kg body weight); and 4 animals received SPLV-entrapped streptomycin in a sterile saline solution (concentration 10 mg streptomycin/kg body weight). All solutions were administered topically into each eye. After 24 hours, the swabbing of conjunctivae of all rabbits was resumed and continued daily for seven days. The results of isolation for *M. bovis* on blood agar plates are shown in Table XV.

9.3. Treatment of Keratoconjunctivitis Resulting from Subcutaneous Infections

*M. bovis* , ATCC strain 10900, were diluted to a concentration of $1\times10^7$ cells per ml in sterile saline. Aliquots (0.1 ml) of bacterial suspensions were inoculated into the eyes of adult rabbits which had been previously infected as described in Section 9.2. and were not treated with SPLVs.

TABLE XV

RESULTS OF ISOLATION FROM RABBIT CONJUNCTIVAE AFTER TOPICALLY INFECTING WITH *M. BOVIS* AND TREATING WITH AQUEOUS OR SPLV-ENCAPSULATED STREPTOMYCIN

| | | *M. bovis* Cultures[a] Days Post-Infection | | | | | | |
|---|---|---|---|---|---|---|---|---|
| | | Pre-Treatment[b] | | Post-Treatment[c] | | | | |
| Group | Animal Number | 1 | 2 | 3 | 4 | 5 | 6 | 7 |
| Control | 1 | 0 | + | + | + | + | + | + |
| | 2 | 0 | + | + | + | + | + | + |
| Streptomycin[d] | 1 | 0 | + | + | + | + | + | + |
| | 2 | 0 | 0 | + | + | + | + | + |
| | 3 | 0 | + | + | + | + | + | + |
| | 4 | 0 | + | + | + | + | + | + |
| SPLV-Entrapped Streptomycin[e] | 1 | 0 | 0 | + | 0 | 0 | 0 | 0 |
| | 2 | 0 | + | + | 0 | 0 | 0 | 0 |
| | 3 | 0 | + | + | 0 | 0 | 0 | 0 |
| | 4 | 0 | + | + | 0 | 0 | 0 | 0 |

[a]Cultures scored for presence of *M. bovis* colonies on blood agar plates after 24 hours at 37° C. Plus (+) represents greater than or equal to 1 CFU *M. bovis* per isolate; 0 represents no detectable colonies.
[b]All animals inoculated with $1\times10^6$ CFU *M. bovis* topically in each eye.
[c]Animals treated with 0.1 ml solution topically in each eye.
[d]Streptomycin (10 mg/kg body weight) in sterile saline solution.
[e]SPLV-entrapped streptomycin (10 mg/kg body weight) in sterile saline solution.

The right eyes of all nine rabbits were inoculated with 0.1 ml of *M. bovis* subcutaneously into conjunctival tissue and in the left eyes of all rabbits were inoculated with 0.1 ml of *M. bovis* topically. Cultures were taken daily from conjunctivae of both eyes from all rabbits and plated onto blood agar plates for isolation of *M. bovis*. Three days post-inoculation, rabbits were divided into 3 groups: 2 animals received no treatment; 3 animals received streptomycin in a standard ophthalmic glycerin suspension (concentration of streptomycin 10 mg/kg body weight); and 4 animals received a saline suspension of SPLV-entrapped streptomycin (10 mg of streptomycin sulfate per kg of body weight). The suspension or solution was administered topically (0.1 ml) into each eye. After 24 hours and on each of the next

TABLE XIV

RESULTS OF TREATMENT OF INFECTIOUS KERATOCONJUNCTIVITIS RESULTING FROM OCULAR INFECTIONS OF *M. BOVIS* IN MICE

| | Number of Mice Per Group of 20 | | | | | | | | | | *M. Bovis* Cultures[a] | |
|---|---|---|---|---|---|---|---|---|---|---|---|---|
| | Pre-Treatment Corneal Opacity[b] | | | | | Post-Treatment Corneal Opacity[b] | | | | | Days Post-Treatment | |
| | 0 | 1 | 2 | 3 | 4 | 0 | 1 | 2 | 3 | 4 | 3 | 5 |
| Non-radiated Mice | | | | | | | | | | | | |
| Controls | 16 | 3 | 0 | 1 | 0 | 18 | 2 | 0 | 0 | 0 | 4/5 | 4/5 |
| Free Streptomycin[c] | 18 | 1 | 1 | 0 | 0 | 18 | 2 | 0 | 0 | 0 | 2/5 | 2/5 |
| Buffer-filled SPLVs plus free Streptomycin[c] | 17 | 2 | 1 | 0 | 0 | 18 | 1 | 1 | 0 | 0 | 2/5 | 3/5 |
| SPLVs-Entrapped Streptomycin[c] | 17 | 3 | 0 | 0 | 0 | 20 | 0 | 0 | 0 | 0 | 0/5 | 0/5 |
| UV-Radiated Mice | | | | | | | | | | | | |
| Controls | 1 | 1 | 5 | 9 | 4 | 10 | 3 | 1 | 2 | 4 | 5/5 | 5/5 |
| Free Streptomycin[c] | 0 | 4 | 9 | 7 | 0 | 14 | 3 | 2 | 1 | 0 | 3/5 | 4/5 |
| Buffer-filled SPLVs plus free Streptomycin[c] | 0 | 3 | 5 | 10 | 2 | 11 | 2 | 4 | 3 | 0 | 3/5 | 3/5 |
| SPLVs-Entrapped Streptomycin[c] | 0 | 1 | 5 | 11 | 3 | 19 | 1 | 0 | 0 | 0 | 0/5 | 0/5 |

[a]Culture of eyes positive for presence of *M. bovis*, determined by fluorescent antibody staining.
[b]Scoring of normal cornea: 1 = loss of normal luster; 2 = small foci of opacity; 3 = partial opacity of cornea; 4 = total opacity of cornea.
[c]Total administration 10 μl (1.0 mg streptomycin per eye).

five days, conjunctival swabbings were taken from all rabbits. The results of isolation for *M. bovis* on blood agar plates are shown in Table XVI. Necropsies were performed on all animals at the termination of experiments and conjunctivae were removed from all animals. These were scored for vascularization, and were minced, homogenized and plated onto blood agar plates for isolation of *M. bovis*. Results are shown in Table XVII.

9.4. Evaluation of the Effectiveness of SPLVs as Compared to Liposome Preparations in the Treatment of ocular Infections

*M. bovis* (ATCC strain 10900) were diluted to a concentration of $1\times10^7$ cells per ml in sterile saline. Aliquots (0.1 ml) of bacterial suspensions were inoculated subcutaneously into the conjunctival tissues of both eyes in adult rabbits. Swabbings were taken daily from conjunctivae of both eyes from all rabbits and plated onto blood agar plates for isolation of *M. bovis*.

TABLE XVI

RESULTS OF ISOLATION FROM RABBIT CONJUNCTIVAE AFTER INOCULATION OF *M. BOVIS* INTO CONJUNCTIVAL MEMBRANES AND TREATMENT WITH STREPTOMYCIN IN OPHTHALMIC GLYCERINE SOLUTION OR SPLV-ENCAPSULATED STREPTOMYCIN IN SALINE

| | | *M. bovis* Cultures[a] Days Post Infection[c] | | | | |
|---|---|---|---|---|---|---|
| | | Pre-treatment | | Post-Treatment | | |
| Group | Animal Number[b] | 1 | 2 | 3 | 4 | 5 |
| Control | 1 | + | + | + | + | + |
| | 2 | + | + | + | + | + |
| Streptomycin | 1 | + | + | + | + | + |
| in Glycerine | 2 | + | + | + | + | + |
| solution[d] | 3 | + | + | + | + | + |
| SPLV- | 1 | + | + | 0 | 0 | 0 |
| Encapsulated | 2 | + | + | 0 | 0 | 0 |
| Streptomycin[e] | 3 | + | + | 0 | 0 | 0 |
| | 4 | + | + | 0 | 0 | 0 |

[a]Cultures scored for presence of *M. bovis* colonies on blood agar plates after 24 hours at 37° C. Plus (+) represents greater than or equal to 1 CFU *M. bovis* per isolate; 0 represents no detectable colonies.
[b]All animals were inoculated with $1\times10^6$ CFU *M. bovis* topically in both eyes; $1\times10^6$ CFU *M. bovis* was injected into conjunctival membranes, in right eyes; and $1\times10^6$ CFU *M. bovis* was applied topically in left eyes.
[c]Animals treated with 0.1 ml solution topically in each eye.
[d]Animals treated topically in each eye with streptomycin (10 mg/kg body weight) in ophthalmic glycerine base.
[e]Animals treated topically in each eye with SPLV-encapsulated streptomycin (10 mg/kg body weight) in sterile saline solution.

TABLE XVII

RESULTS FROM NECROPSY OF THE ORBIT AND ASSOCIATED TISSUES FROM RABBITS AFTER INOCULATION WITH *M. BOVIS* INTO CONJUNCTIVAL TISSUES AND TREATMENT WITH EITHER STREPTOMYCIN IN OPHTHALMIC GLYCERINE SOLUTION OR SPLV-ENCAPSULATED STREPTOMYCIN IN STERILE SALINE[a]

| | Isolation of *M. bovis* Cultures | Vascularization of Right Eye[b] |
|---|---|---|
| Control | | |
| A | + | 2+ |
| B | + | 2+ |
| Streptomycin in Glycerine Solution | | |
| A | + | 2+ |
| B | + | 1+ |
| C | + | 2+ |
| D | + | 2+ |
| SPLV-encapsulated Streptomycin | | |
| A | 0 | 0 |
| B | 0 | 0 |
| C | 0 | 0 |
| D | 0 | 0 |

[a]Legends are same as Table XII, performed on day 5, post infection.
[b]Vascularization scored as follows: 0 = vessels normal; 1 = some vessels definitely dilated and infiltrated by minor vessels; 2 = diffuse red with individual vessels not easily discernible; 3 = diffuse beefy red, vascular leakage and effusion of blood into conjunctivae.

Five days post-inoculation, rabbits were divided into 6 groups: 2 animals received no treatment (controls); 3 animals received a suspension of SPLV-encapsulated streptomycin (10 mg of streptomycin sulfate per kg of body weight) which when diluted 1:100 had an $O.D._{480}$ (optical density at 480 nm) equal to 0.928; 3 animals received a suspension of SPLV-encapsulated streptomycin (10 mg of streptomycin sulfate per kg of body weight) which when diluted 1:100 had an $O.D._{480}$ equal to 0.449; 3 animals received a suspension of SPLV-encapsulated streptomycin (10 mg streptomycin sulfate per kg of body weight) which when diluted 1:100 had an $O.D._{480}$ equal to 0.242; 3 animals received a suspension of SPLV-encapsulated streptomycin (10 mg streptomycin sulfate per kg body weight) which when diluted 1:100 had an $O.D._{480}$ equal to 0.119; and 2 animals received a suspension of multilamellar vesicles (MLVs) containing streptomycin (10 mg streptomycin sulfate per kg of body weight) with an $O.D._{480}$ of a 1:100 dilution equal to 0.940. MLVS were made by the process of Fountain et al. Curr. Micro. 6:373 (1981) by adding streptomycin sulfate to the dried lipid film which was then vortexed, and allowed to swell for two hours; the non-entrapped streptomycin was removed by repeated centrifugation.

The suspensions were administered topically into each eye. After 24 hours, conjunctival swabbings were taken from all rabbits daily for 9 days and plated onto blood agar. The results of isolation for *M. bovis* on blood agar plates are shown in Table XVIII. Necropsies were performed on all animals. These were scored for lacrimal secretions, and conjunctivae were removed aseptically from all animals. These were scored for vascularization, and were minced, homogenized and plated onto blood agar plates for isolation of *M. bovis*. Results are shown in Table XIX.

10. EXAMPLE: TREATMENT OF VIRAL INFECTIONS

Lymphocytic choriomeningitis virus (LCMV), a member of the Arenavirus group, is known to cause diseases in man and LCMV infection is fatal in mice inoculated intracerebrally with this virus. The death of mice is caused by the immune cells which react against virus-infected cells. The virus does not kill the cells in which it multiplies, therefore, the therapeutic agent used in mice must either inhibit virus multiplication so that the immune cells will not be activated, and/or inhibit the activation of immune cells.

The following example demonstrates the effectiveness of treating viral infections by administering a SPLV-encapsulated antiviral compound.

10.1. Treatment of Lethal Lymphocytic Choriomeningitis Virus Infections in Mice Swiss mice 2 months of age were inoculated intracerebrally with a lethal dose of LCM virus, i.e., 100 plaque forming units (PFU) in 0.05 ml inoculum per mouse. Mice were divided into 4 groups of 7 animals each and were treated on days 2, 3 and 4 post-infection by intraperitoneal injections with 0.1 ml/dose/mouse as follows: (1) the "SPLV-R group" was treated with a suspension of egg phosphatidylcholine SPLVs containing 3 mg Ribavarin/ml.

TABLE XVIII

ISOLATION OF *M. BOVIS* FROM INFECTED RABBIT CONJUNCTIVAE AFTER TREATMENT WITH DILUTIONS OF SPLV-ENCAPSULATED STREPTOMYCIN IN SALINE OR MLV-ENCAPSULATED STREPTOMYCIN IN SALINE

| | | Isolation of *M. bovis*[a] Days Post-Infection | | | | | | | | | | | | | |
|---|---|---|---|---|---|---|---|---|---|---|---|---|---|---|---|
| | Animal | Pre-Treatment | | | | | Post-Treatment | | | | | | | | |
| Group | Number | 1 | 2 | 3 | 4 | 5 | 6 | 7 | 8 | 9 | 10 | 11 | 12 | 13 | 14 |
| Control | 1 | + | + | + | + | + | + | + | + | + | + | + | + | + | + |
| | 2 | + | + | + | + | + | + | + | + | + | + | + | + | + | + |
| MLV- | 1 | + | + | + | + | + | + | + | 0 | 0 | + | + | + | 0 | + |
| encapsulated | 2 | + | + | + | + | + | + | 0 | + | + | 0 | 0 | + | + | 0 |
| Streptomycin | | | | | | | | | | | | | | | |
| SPLV- | 1 | + | + | + | + | + | 0 | 0 | 0 | 0 | 0 | 0 | 0 | 0 | 0 |
| encapsulated | 2 | + | + | + | + | + | 0 | 0 | 0 | 0 | 0 | 0 | 0 | 0 | 0 |
| Streptomycin | 3 | + | + | + | + | + | 0 | 0 | 0 | 0 | 0 | 0 | 0 | 0 | 0 |
| (undiluted) | | | | | | | | | | | | | | | |
| SPLV- | 1 | + | + | + | + | + | + | 0 | + | + | + | + | + | + | + |
| encapsulated | 2 | + | + | + | + | + | 0 | 0 | + | 0 | 0 | 0 | 0 | 0 | 0 |
| Streptomycin | 3 | + | + | + | + | + | 0 | 0 | 0 | 0 | + | 0 | 0 | 0 | 0 |
| (1:2 dilution) | | | | | | | | | | | | | | | |
| SPLV- | 1 | + | + | + | + | + | + | + | 0 | 0 | 0 | 0 | 0 | 0 | 0 |
| encapsulated | 2 | + | + | + | + | + | + | 0 | 0 | 0 | + | 0 | 0 | 0 | 0 |
| Streptomycin | 3 | + | + | + | + | + | 0 | 0 | + | + | + | + | + | + | + |
| (1:4 dilution) | | | | | | | | | | | | | | | |
| SPLV- | 1 | + | + | + | + | + | 0 | 0 | + | + | + | + | + | + | + |
| encapsulated | 2 | + | + | + | + | + | 0 | 0 | 0 | 0 | 0 | 0 | 0 | 0 | 0 |
| Streptomycin | 3 | + | + | + | + | + | + | + | + | 0 | + | + | + | + | + |
| (1:6 dilution) | | | | | | | | | | | | | | | |

[a]All animals inoculated with $1 \times 10^6$ CFU *M. bovis* by injection into conjunctival membranes of both eyes. Conjunctival swabbings were plated on blood agar. Cultures scored for presence of *M. bovis* colonies on blood agar plates after 24 hours at 37° C.; + = greater than or equal to 1 CFU; 0 = no detectable cultures.

TABLE XIX

RESULTS FROM NECROPSY OF THE ORBIT AND ASSOCIATED TISSUES FROM RABBITS AFTER INOCULATION WITH *M. BOVIS* INTO CONJUNCTIVAL TISSUES AND TREATMENT WITH EITHER MLV-ENCAPSULATED STREPTOMYCIN, SPLV-ENCAPSULATED STREPTOMYCIN OR DILUTIONS OF SPLV-ENCAPSULATED STREPTOMYCIN[a]

| | Animal | Isolation of *M. Bovis* | Vascularization of Eyes[b] | Lacrimal Discharge[c] |
|---|---|---|---|---|
| Control | 1 | + | 1+ | 1+ |
| | 2 | + | 1+ | 1+ |
| MLV- | 1 | + | 1+ | 1+ |
| encapsulated | 2 | 0 | 1+ | 0 |
| Streptomycin | | | | |
| SPLV- | 1 | 0 | 0 | 0 |
| encapsulated | 2 | 0 | 1+ | 0 |
| Streptomycin | 3 | 0 | 0 | 0 |
| (undiluted) | | | | |
| SPLV- | 1 | + | 2+ | 2+ |
| encapsulated | 2 | 0 | 0 | 0 |
| Streptomycin | 3 | 0 | 1+ | 0 |
| (1:2 dilution) | | | | |
| SPLV- | 1 | 0 | 0 | 0 |
| encapsulated | 2 | 0 | 1+ | 0 |
| Streptomycin | 3 | + | 1+ | 0 |
| (1:4 dilution) | | | | |

TABLE XIX-continued

RESULTS FROM NECROPSY OF THE ORBIT AND ASSOCIATED TISSUES FROM RABBITS AFTER INOCULATION WITH *M. BOVIS* INTO CONJUNCTIVAL TISSUES AND TREATMENT WITH EITHER MLV-ENCAPSULATED STREPTOMYCIN, SPLV-ENCAPSULATED STREPTOMYCIN OR DILUTIONS OF SPLV-ENCAPSULATED STREPTOMYCIN[a]

| | Animal | Isolation of *M. Bovis* | Vascularization of Eyes[b] | Lacrimal Discharge[c] |
|---|---|---|---|---|
| SPLV- | 1 | + | 1+ | 1+ |
| encapsulated | 2 | 0 | 1+ | 0 |
| Streptomycin | 3 | + | 1+ | 0 |
| (1:6 dilution) | | | | |

[a]Legends are same as Table XIV, performed on day 14 post-infection.
[b]Vascularization scored as follows: 0 = vessels normal; 1 = some vessels dilated and infiltrated by minor vessels; 2 = diffuse red with individual vessels not easily discernable; 3 = diffuse beefy red, vascular leakage and effusion of blood into conjunctivae.
[c]Discharge scored as follows: 0 = no discharge; 1 = discharge with moistening of lids and hairs adjacent to lids; 2 = discharge with moistening of lids, hairs and areas adjacent to eyes.

TABLE XX

TREATMENT OF LETHAL LCM VIRUS INFECTION IN MICE[a]

| Group | Lethality[c] | Virus Recovered from Spleen (PFU $\times 10^5$/ml)[c] |
|---|---|---|
| Control | 5/5 | 7.0 |
| SPLV-group | 5/5 | 6.9 |
| R-group | 5/5 | 5.2 |
| SPLV-R-Group | 3/5 | 3.4 |

[a]Two month old mice were each inoculated intracerebrally with a lethal dose, i.e., 100 PFU of LCM virus in 0.05 ml inocula.
[b]Lethality is expressed as number dead/number in group.
[c]On the fifth day post-infection 2 mice from each group were sacrificed and their spleens homogenized at a concentration of 1 gm spleen/20 ml homogenate.

SPLVs were prepared using 100 mg lipids and 0.3 ml of 100 mg drug/ml in PBS buffer; the entrapment of drug was 10%; (2) the-"R-group" was treated with a solution of Ribavarin 3 mg/ml in PBS; (3) the "SPLV-group" was treated with buffer-filled SPLVs (i.e., SPLVs prepared as above but without Ribavarin); and (4) the "control group" was treated with PBS. On day 5 postinfection 2 mice from each group were sacrificed and their spleens homogenized (2 spleens/group were homogenized in PBS at 1/20 weight per volume buffer). The plague forming units (PFU) per ml were determined for each suspension. The remaining 5 mice in each groups were observed for lethality two times daily for 30 days. The results are presented in Table XX.

Table XX clearly indicates a decrease in lethality and a decrease in the virus recoverable from the infected animals. We have not yet determined whether these results are due to the anti-viral activity of the ribavarin which is released from the SPLVs or whether it is due to an immunomodulation of the mouse host during the sustained release of ribavarin from the SPLVs.

What is claimed is:

1. A method for preparing stable plurilamellar vesicles, comprising:

(a) forming a dispersion of at least one amphipathic lipid in an organic solvent;

(b) combining the dispersion with a sufficient amount of an aqueous phase to form a biphasic mixture in which the aqueous phase can be completely emulsified; and (c) concurrently emulsifying the aqueous phase while evaporating the organic solvent of the biphasic mixtures, wherein the stable plurilamellar vesicles produced are substantially free of MLVs, SUVs, and REVs.

2. The method according to claim 1, wherein the ratio of volume of solvent to volume of aqueous phase is from about 3:1 to about 100:1.

3. The method according to claim 1, wherein the temperature at which the method is performed is from about 4° C. to about 60° C.

4. The method according to claim 1, wherein the temperature at which the method is performed is less than the phase transition temperature of at least one of said lipids.

5. The method according to claim 1, wherein the solvent is fluorocarbon or diethylether, or mixtures thereof.

6. The method according to claim 5 wherein the solvent contains an anti-oxidant.

7. The method according to claim 6, wherein said anti-oxidant is butylated hydroxytoluene.

8. The method according to claim 1 wherein a material to be entrapped in the vesicles is added with the aqueous phase.

9. The method according to claim 8, wherein at least 20 percent of said material is entrapped in the vesicles.

10. The method according to claim 8, wherein said material is a protein.

11. Stable plurilamellar vesicles comprising lipid vesicles ranging from about 1OO nm to about 10,000 nm in size, characterized by a few to over 100 lipid bilayers enclosing aqueous compartments containing at least one entrapped solute in which the lipid bilayers have an ordered molecular architecture creating a supramolecular structure which differs from that of other multilamellar vesicles so that when compared to other multilamellar vesicles composed of the identical lipid and aqueous ingredients, stable plurilamellar vesicles have the following properties:

(a) a higher percent entrapment of solute;

(b) a lower buoyant density;

(c) a volume about one-third larger;

(d) greater stability to auto-oxidation during storage in buffer;

(e) greater stability in body fluids;

(f) a larger percent leakage of entrapped solute when exposed to urea, guanidine, or ammonium acetate;

(g) a smaller percent leakage of entrapped solute when exposed to hydrochloric acid or serum; and (h) distribution of entrapped contents throughout the cytosol of cells when administered to the cells in culture.

12. Stable plurilamellar vesicles according to claim 11 substantially free of MLVs, SUVs, and REVs.

13. The stable plurilumellar vesicles of claim 11 in which the lipid bilayers comprise a phospholipid.

14. The stable plurilamellar vesicles of claim 13 in which the phospholipid is amphipathic.

15. Stable plurilamellar vesicles according to claim 11, wherein the major lipid component of the vesicles is a phosphatidylcholine.

16. Stable plurilamellar vesicles according to claim 11, wherein an anti-oxidant is a component of the vesicle.

17. Stable plurilamellar vesicles according to claim 16 wherein said anti-oxidant is butylated hydroxytoluene.

18. Stable plurilamellar vesicles according to claim 12, wherein a protein is entrapped within the vesicle.

19. Stable plurilamellar vesicles according to claim 12, wherein a compound selected from the group consisting of: antibacterial compounds, antifungal compounds, antiparasitic compounds, and antiviral compounds is entrapped within the vesicle.

20. Stable plurilamellar vesicles according to claim 11, wherein a compound selected from the group consisting of: tumoricidal compounds, toxins, cell receptor binding molecules, and immunoglobulins is entrapped within the vesicle.

21. Stable plurilamellar vesicles according to claim 11, wherein a compound selected from the group consisting of: anti-inflammatory compounds, anti-glaucoma compounds, mydriatic compounds, and local anesthetics is entrapped within the vesicle.

22. Stable plurilamellar vesicles according to claim 11, wherein a compound selected from the group consisting of: enzymes, hormones, neurotransmitters, immunomodulators, nucleotides, and cyclic adenosine monophosphate is entrapped within the vesicle.

23. Stable plurilamellar vesicles according to claim 11, wherein a compound selected from the group consisting of: dyes, fluorescent compounds, radioactive compounds, and radio-opaque compounds is entrapped within the vesicle.

24. A method for delivery of a compound to cells in vivo, comprising: administering to an organism stable plurilamellar vesicles of claim 11 containing said compound entrapped therein.

25. The method according to claim 24, wherein said stable plurilamellar vesicles are administered topically, intraperitoneally, intravenously, intramuscularly, subcutaneously or intraauricularly.

26. A method for treatment of infections in animals or plants, comprising: administering stable plurilamellar vesicles of claim 11 containing a compound effective for treating said infection.

27. The method according to claim 26, wherein said infection is intracellular.

28. The method according to claim 27 wherein said infection is caused by a parasite.

29. The method according to claim 28, wherein said infection is caused by Brucella spp.

30. The method according to claim 29, wherein said administration is intraperitoneal.

31. The method according to claim 26, wherein said infection is extracellular.

32. The method according to claim 31 wherein said infection is caused by bacteria.

33. The method according to claim 32, wherein said infection is caused by *Staphylococcus aureus*.

34. The method according to claim 33, wherein said administration is intraperitoneal.

35. The method according to claim 26, wherein said infection is an ocular infection.

36. The method according to claim 35, wherein said infection is caused by a Moraxella spp.

37. The method according to claim 36, wherein said administration is topical.

38. The method according to claim 26, wherein said infection is caused by a virus.

39. The method according to claim 38, wherein said infection is caused by lymphocytic choriomeningitis virus.

40. The method according to claim 39, wherein said administration is intraperitoneal.

41. A method for treatment of afflictions in animals or plants requiring sustained release of a compound effective for treating said affliction, comprising: administering stable plurilamellar vesicles of claim 11 containing said compound.

42. The method according to claim 41, wherein said affliction is an ocular affliction.

43. A method according to claim 42, wherein said affliction is glaucoma.

44. The method according to claim 43, wherein said administration is topical.

* * * * *